US011484658B2

(12) United States Patent  
Steel et al.

(10) Patent No.: US 11,484,658 B2
(45) Date of Patent: Nov. 1, 2022

(54) PEN TYPE DRUG INJECTION DEVICE WITH ABSOLUTE ANGULAR DOSE ENCODER MECHANISM

(71) Applicant: Sanofi-Aventis Deutschland GMBH, Frankfurt am Main (DE)

(72) Inventors: Samuel Keir Steel, Warwickshire (GB); Paul Richard Draper, Worcestershire (GB); George Cave, Warwickshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 202 days.

(21) Appl. No.: 16/847,262

(22) Filed: Apr. 13, 2020

(65) Prior Publication Data

US 2020/0306455 A1    Oct. 1, 2020

Related U.S. Application Data

(63) Continuation of application No. 14/761,080, filed as application No. PCT/EP2014/050470 on Jan. 13, 2014, now Pat. No. 10,653,847.

(30) Foreign Application Priority Data

Jan. 15, 2013  (EP) .................................. 13151374

(51) Int. Cl.
*A61M 5/315* (2006.01)
*G01D 5/165* (2006.01)
(Continued)

(52) U.S. Cl.
CPC ...... *A61M 5/31546* (2013.01); *A61M 5/3155* (2013.01); *A61M 5/3158* (2013.01);
(Continued)

(58) Field of Classification Search
CPC ............ A61M 5/31535; A61M 5/3155; A61M 5/31551; A61M 5/3158; A61M 5/31568;
(Continued)

(56) References Cited

U.S. PATENT DOCUMENTS 533,575 A    2/1895  Wilkens
5,226,895 A  7/1993  Harris
(Continued)

FOREIGN PATENT DOCUMENTS

CN    101268336    9/2008
CN    101421913    4/2009
(Continued)

OTHER PUBLICATIONS

International Search Report and Written Opinion in International Application No. PCT/EP2014/050470, dated May 28, 2014, 14 pages.
(Continued)

*Primary Examiner* — Dung T Ulsh
(74) *Attorney, Agent, or Firm* — Fish & Richardson P.C.

(57) ABSTRACT

A drug delivery device comprising: a housing; a cylindrical member rotatably supported within the housing; and a plurality of sensors; wherein: the outer surface of the cylindrical member is provided with a single track, the track forming an encoder and having a plurality of first track segments and a plurality of second track segments arranged along the length of the track which are respectively capable of inducing first and second responses in the sensors; and in each rotational position of the cylindrical member relative to the housing at least one different first track segment is capable of inducing a first response in at least one said sensor, thereby enabling the rotational position of the cylindrical member relative to the housing to be determined.

14 Claims, 16 Drawing Sheets

(51) Int. Cl.
*G01D 5/347* (2006.01)
*A61M 5/31* (2006.01)

(52) U.S. Cl.
CPC .... *A61M 5/31525* (2013.01); *A61M 5/31535* (2013.01); *A61M 5/31551* (2013.01); *A61M 5/31556* (2013.01); *G01D 5/1655* (2013.01); *G01D 5/34746* (2013.01); *A61M 5/31568* (2013.01); *A61M 2005/3125* (2013.01); *A61M 2005/3126* (2013.01); *A61M 2205/3306* (2013.01); *A61M 2205/3317* (2013.01); *A61M 2205/6063* (2013.01); *G01D 5/34792* (2013.01)

(58) Field of Classification Search
CPC .. A61M 2005/3125; A61M 2005/3126; A61M 2205/3306; A61M 2205/3317
See application file for complete search history.

(56) References Cited

U.S. PATENT DOCUMENTS

| | | | |
|---|---|---|---|
| 5,279,586 | A | 1/1994 | Balkwill |
| 5,304,152 | A | 4/1994 | Sams |
| 5,320,609 | A | 6/1994 | Haber et al. |
| 5,383,865 | A | 1/1995 | Michel |
| 5,480,387 | A | 1/1996 | Gabriel et al. |
| 5,505,704 | A | 4/1996 | Pawelka et al. |
| 5,582,598 | A | 12/1996 | Chanoch |
| 5,626,566 | A | 5/1997 | Petersen et al. |
| 5,674,204 | A | 10/1997 | Chanoch |
| 5,688,251 | A | 11/1997 | Chanoch |
| 5,921,966 | A | 7/1999 | Bendek et al. |
| 5,961,495 | A | 10/1999 | Walters et al. |
| 6,004,297 | A | 12/1999 | Steenfeldt-Jensen et al. |
| 6,193,698 | B1 | 2/2001 | Kirchhofer et al. |
| 6,221,046 | B1 | 4/2001 | Burroughs et al. |
| 6,235,004 | B1 | 5/2001 | Steenfeldt-Jensen et al. |
| 6,248,095 | B1 | 6/2001 | Giambattista et al. |
| 6,899,698 | B2 | 5/2005 | Sams |
| 6,936,032 | B1 | 8/2005 | Bush, Jr. et al. |
| 7,241,278 | B2 | 7/2007 | Moller |
| 8,197,449 | B2 * | 6/2012 | Nielsen ............... A61M 5/3155 604/207 |
| 8,638,108 | B2 | 1/2014 | Nielsen et al. |
| 8,974,413 | B2 | 3/2015 | Baba et al. |
| 9,186,465 | B2 | 11/2015 | Jorgensen et al. |
| 9,220,845 | B2 | 12/2015 | Atterbury et al. |
| 2002/0052578 | A1 | 5/2002 | Moller |
| 2002/0120235 | A1 | 8/2002 | Engaard |
| 2003/0050609 | A1 | 3/2003 | Sams |
| 2004/0059299 | A1 | 3/2004 | Moller |
| 2004/0210199 | A1 | 10/2004 | Atterbury et al. |
| 2004/0267207 | A1 | 12/2004 | Veasey et al. |
| 2005/0113765 | A1 | 5/2005 | Veasey et al. |
| 2006/0153693 | A1 | 7/2006 | Fiechter et al. |
| 2006/0224123 | A1 * | 10/2006 | Friedli .............. A61M 5/31525 604/207 |
| 2007/0123829 | A1 * | 5/2007 | Atterbury ............ G01D 5/2497 604/207 |
| 2009/0076460 | A1 | 3/2009 | Nielsen et al. |
| 2009/0275916 | A1 | 11/2009 | Harms et al. |
| 2011/0181301 | A1 | 7/2011 | Nielsen et al. |
| 2011/0270214 | A1 | 11/2011 | Jorgensen et al. |

FOREIGN PATENT DOCUMENTS

| | | |
|---|---|---|
| CN | 102202711 | 9/2011 |
| EP | 0937471 | 8/1999 |
| EP | 0937476 | 8/1999 |
| EP | 1095668 | 5/2001 |
| EP | 2275158 | 5/2002 |
| JP | 2005/508205 | 3/2005 |
| JP | 2009/508608 | 3/2009 |
| JP | 2012/507314 | 9/2012 |
| WO | WO 99/38554 | 8/1999 |
| WO | WO 01/10484 | 2/2001 |
| WO | WO 03/057286 | 7/2003 |
| WO | WO 2005/053778 | 6/2005 |
| WO | WO 2006/037434 | 4/2006 |
| WO | WO 2006/040296 | 4/2006 |
| WO | WO 2006/084876 | 8/2006 |
| WO | WO 2006/120182 | 11/2006 |
| WO | WO 2008/148540 | 12/2008 |
| WO | WO 2009/132778 | 11/2009 |
| WO | WO 2013/004843 | 1/2013 |
| WO | WO 2013/004844 | 1/2013 |

OTHER PUBLICATIONS

International Preliminary Report on Patentability in International Application No. PCT/EP2014/050470, dated Jul. 21, 2015, 9 pages.
Extended European Search Report Issued in European Patent Application No. 17159671.1, dated Feb. 20, 2018.
English Translation of the Search Report issued in Chinese Patent Application No. 2014-0004496.8, dated Apr. 25, 3017.
Track Webster Definition.

* cited by examiner

| Position '0'<br>zero dose dialled<br>First output: 1000001 | Position '1'<br>x dose units dialled<br>Second output: 0000011 | Position '2'<br>y dose units dialled<br>Third output: 0000110 |
|---|---|---|
| Contact 1  1<br>Contact 2  0<br>Contact 3  0<br>Contact 4  0<br>Contact 5  0<br>Contact 6  0<br>Contact 7  1<br>1<br>0<br>0<br>0<br>0<br>1<br>0<br>1<br>0<br>0<br>0<br>0<br>1<br>1<br>1<br>.<br>.<br>. | 1<br>0<br>0<br>0<br>0<br>1<br>1<br>0<br>0<br>0<br>0<br>1<br>0<br>1<br>0<br>0<br>0<br>0<br>1<br>1<br>1<br>.<br>.<br>. | 1<br>0<br>0<br>0<br>0<br>1<br>1<br>0<br>0<br>0<br>0<br>1<br>0<br>1<br>0<br>0<br>0<br>0<br>1<br>1<br>1<br>.<br>.<br>. |

Seven contacts

PEN TYPE DRUG INJECTION DEVICE WITH ABSOLUTE ANGULAR DOSE ENCODER MECHANISM

CROSS REFERENCE TO RELATED APPLICATIONS

The present application is a continuation of U.S. patent application Ser. No. 14/761,080, filed on Jul. 15, 2015, which is a U.S. National Phase Application pursuant to 35 U.S.C. § 371 of International Application No. PCT/EP2014/050470 filed Jan. 13, 2014, which claims priority to European Patent Application No. 13151374.9 filed Jan. 15, 2013. The entire disclosure contents of these applications are herewith incorporated by reference into the present application.

FIELD OF INVENTION

The present invention relates to a drug delivery device.

BACKGROUND

Pen type drug delivery devices have application where regular injection by persons without formal medical training occurs. This is increasingly common among patients having diabetes where self-treatment enables such patients to conduct effective management of their diabetes.

For good or perfect glycemic control, the dose of insulin or insulin glargine has to be adjusted for each individual in accordance with a blood glucose level to be achieved. The present invention relates to injectors, for example hand-held injectors, especially pen-type injectors, that is to injectors of the kind that provide for administration by injection of medicinal products from a multidose cartridge. In particular, the present invention relates to such injectors where a user may set the dose.

A user undertaking self-administration of insulin will commonly need to administer between 1 and 80 International Units.

SUMMARY

According to an aspect of the invention there is provided a drug delivery device comprising: a housing; a cylindrical member rotatably supported within the housing; and a plurality of sensors; wherein: the outer surface of the cylindrical member is provided with a single track, the track forming an encoder and having a plurality of first track segments and a plurality of second track segments arranged along the length of the track which are respectively capable of inducing first and second responses in the sensors; and in each rotational position of the cylindrical member relative to the housing at least one different first track segment is capable of inducing a first response in at least one said sensor, thereby enabling the rotational position of the cylindrical member relative to the housing to be determined.

Advantageously, this enables the absolute rotational position of the cylindrical member relative to the housing to be determined using a single track.

The cylindrical member may be supported within the housing and configured to be rotated relative to the housing and the sensors.

The cylindrical member may be movable along a helical path between a plurality of discrete positions. Preferably, each discrete position is being associated with a specific dose amount.

In each discrete position of the cylindrical member the sensors are respectively capable of having induced therein a first or second response by one said first or second track segment.

In each of the discrete positions of the cylindrical member a unique combination of first and second responses is capable of being induced across the plurality of sensors.

Each discrete position of the sensors along the track may be associated with a unique binary code.

The plurality of sensors may be arranged along a single track. The plurality of sensors may be configured to enable interaction with unique configurations of first and second track segments. Preferably, the plurality of sensors interacts with unique configurations of first and second track segments whenever an increment of insulin is dialled or dispensed.

The device may further comprise a processor configured to determine the rotational position of the cylindrical member relative to the housing by analysing signals output from each of the sensors which correspond with whether a first said response or a second said response is induced in a respective said sensor.

The sensors may each comprise an electrical contact, and the first and second track segments may respectively have lower and higher values of electrical resistance, the first track segments being electrically coupled to one another.

The processor may be configured to cause an electrical signal to be applied to one of the electrical contacts while simultaneously detecting whether any of the other electrical contacts are energised, thereby enabling the rotational position of the cylindrical member relative to the housing to be determined.

The processor may be configured to cause an electrical signal to be applied to each of the first track segments via an additional electrical contact while simultaneously detecting whether any of the other electrical contacts are energised, thereby enabling the rotational position of the cylindrical member relative to the housing to be determined.

Advantageously, this enables the absolute rotational position of the cylindrical member relative to the housing to be directly determined by analysing which of the electrical contacts are energised.

The additional electrical contact may engage a section of the track which electrically couples the first track segments to one another.

The device may further comprise an additional track located adjacent the track forming said encoder, said additional track being electrically conductive and in engagement with a further electrical contact, wherein the processor may be configured to analyse signals from the further electrical contact to determine the operational mode of said device.

Advantageously, this enables whether the device is in dialling mode or drug dispensing mode to be determined.

The device may further comprise a switch configured to electrically couple the two tracks in one operational mode of said device, and to electrically decouple the two tracks in another operational mode of said device.

The device may further comprise a delivery button configured to cause expulsion of a drug from the drug delivery device upon actuation thereof by a user, wherein depression of the delivery button changes a state of the switch.

The sensors may each comprise an optical sensor, and the first and second track segments may respectively comprise differently coloured parts of said track.

The processor may be configured to determine which of said optical sensors are directed towards a first track segment and which of said optical sensors are directed towards a second track segment, thereby enabling the rotational position of the cylindrical member relative to the housing to be determined.

Advantageously, this enables the absolute rotational position of the cylindrical member relative to the housing to be directly determined by analysing which types of track segment the optical sensors are directed towards.

The device may further comprise a sleeve which surrounds at least part of said cylindrical member and which rotates relative to the optical sensors in one operational mode of the device but not in another operational mode of the device, and an additional optical sensor for use in monitoring the rotational position of opaque markings provided on the sleeve in order to determine the mode of operation of the device.

Advantageously, this enables whether the device is in dialling mode or drug dispensing mode to be determined.

The processor may be configured to determine a selected drug dose by searching a lookup table stored in a memory, the lookup table providing a conversion between a rotational position of the cylindrical member relative to the housing and a selected drug dose.

The processor may be configured to determine a delivered drug dose by subtracting a remaining drug dose from the selected drug dose.

BRIEF DESCRIPTION OF THE DRAWINGS

Embodiments will now be described, by way of example only, with reference to the accompanying drawings, in which:

FIG. 10 shows a graphical representation of the contacts 212a-212g in FIG. 8 (depicted as contacts 1 to 7) as they move over a coded strip 300;

FIG. 11 shows a numerical representation of the coded strip 300 in FIG. 9;

DETAILED DESCRIPTION

Figure 1:
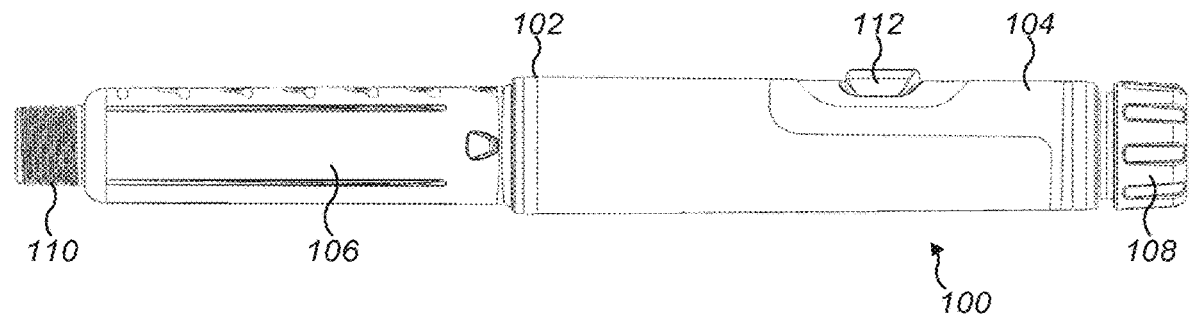
FIG. 1 shows an external view of a drug delivery device 100 suitable for implementing the present invention.

Referring firstly to FIG. 1, an external view of a drug delivery device 100 according to embodiments of the invention is shown. The device 100 shown in FIG. 1 is a pen type injection device, having an elongate cylindrical shape, for setting and delivering a medicament, such as insulin. The device 100 comprises a housing 102 having a first housing part 104 and a second housing part 106. A rotatable dial 108 is located at a first (or proximal) end of the first housing part 104. The rotatable dial 108 has substantially the same outer diameter as the first housing part 104. The second housing part 106 may be detachably connected to the second end of the first housing part 104. The second housing part 106 is configured to have a needle (not shown) or similar drug delivery apparatus attached to it. To achieve this, the second (or distal) end of the second housing part 106 may have a threaded portion 110. The threaded portion 110 may have a smaller diameter than the remainder of the second housing part 106.

A display mount 112 is located on the first housing part 104. A display may be supported on the display mount 112. The display may be an LCD display, a segmented display or any other suitable type of display. The display mount 112 may cover a recess (not shown) in the first housing portion 104. A number of electronic components, described in greater detail with reference to FIG. 2, may be disposed underneath the display mount 112.

The first housing part 104 contains a drug dose setting and delivery mechanism. The second housing part 106 contains a drug cartridge (not shown). The drug contained in the drug cartridge may be a medicament of any kind and may preferably be in a liquid form. The drug delivery mechanism of the first housing part 104 may be configured to engage with the drug cartridge of the second housing part 106 to facilitate expulsion of the drug. The second housing part 106 may be detached from the first housing part 104 in order to insert a drug cartridge or to remove a used cartridge. The first and second housing parts 104, 106 may be connected together in any suitable way, for example with a screw or bayonet type connection. The first and second housing parts 104, 106 may be non-reversibly connected together in such a way that the drug cartridge is permanently contained within the drug delivery device 100. Further the first and second housing parts 104, 106 may form part of a single housing part.

The rotatable dial 108 is configured to be rotated by hand by a user of the drug delivery device 100 in order to set a drug dose to be delivered. The dial 108 may be connected to an internal threading system which causes the dial 108 to be displaced axially from the housing 102 as it is rotated in a first direction. The dial 108 may be rotatable in both directions or only in a first direction. The device 100 is configured, once a drug dose has been set by rotation of the rotatable dial 108, to deliver the set drug dose when a user exerts an axial force at the proximal end of the device. The rotatable dial 108 may support a dose delivery button (416 in FIG. 3) which must be depressed in order to deliver the set drug dose. The display 112 may be configured to display information concerning the drug dose which has been set and/or delivered. The display 112 may further show additional information, such as the actual time, the time of the last usage/injection, a remaining battery capacity, one or more warning signs indicating that a dialled dose has not been fully dispensed, and/or the like.

Figure 2:
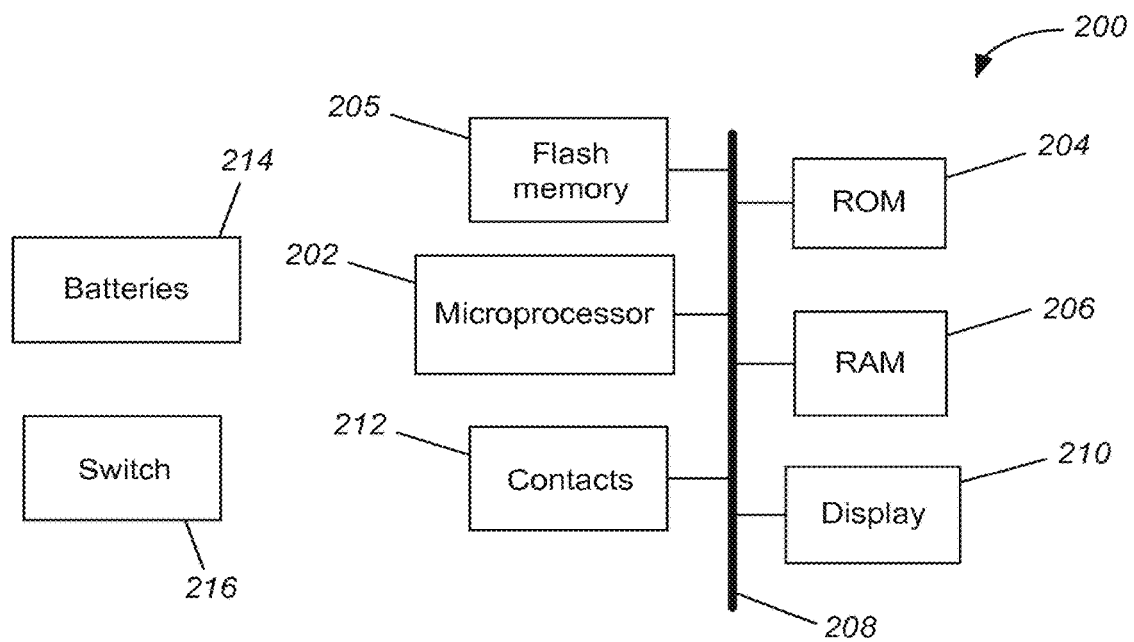
FIG. 2 shows a schematic diagram of some of the electronic components present in the drug delivery device 100 of FIG. 1.

Referring now to FIG. 2, a schematic diagram of electrical circuitry 200 forming part of the drug delivery device 100 is shown. The circuitry 200 comprises a processor 202, a non-volatile memory such as a ROM 204, a writable non-volatile memory such as flash memory 205, a volatile memory such as a RAM 206, a display 210, contacts 212 (described later on as contacts 212a-212i) and a bus 208 connecting each of these components. The circuitry 200 also comprises batteries 214 or some other suitable source of power for providing power to each of the components and a switch 216, described in greater detail below.

The circuitry 200 may be integral with the device 100. Alternatively, the circuitry 200 may be contained within an electronic module that can be attached to the device 100. In addition, the circuitry 200 may comprise additional sensors, such as optical or acoustical sensors. The circuitry 200 may comprise an audible alarm (not shown) which the processor 202 may control to sound an alarm when a dialled dose has not been fully dispensed.

The ROM 204 may be configured to store software and/or firmware. This software/firmware may control operations of the processor 202. The processor 202 utilises RAM 206 to execute the software/firmware stored in the ROM to control operation of the display 210. As such the processor 202 may also comprise a display driver. The processor 202 utilises the flash memory 205 to store determined amounts of dose dialled and/or determined amounts of dose dispensed, as will be described in more detail below.

The batteries 214 may provide power for each of the components including the contacts 212. The supply of electricity to the contacts 212 may be controlled by the processor 202. The processor 202 may receive signals from the contacts 212 and so could determine when the contacts are energised, and is configured to interpret these signals. Information may be provided on the display 210 at suitable times by operation of the software/firmware and the processor 202. This information may include measurements determined from the signals received by the processor 202 from the contacts 212.

A number of contacts 212 may be present in the device 100. For example, seven contacts 212 may be present and may be addressed individually by the processor. In other embodiments, eight or nine contacts 212 are present. The contacts 212 may be mounted on an inner surface of the housing 102.

Figure 3:
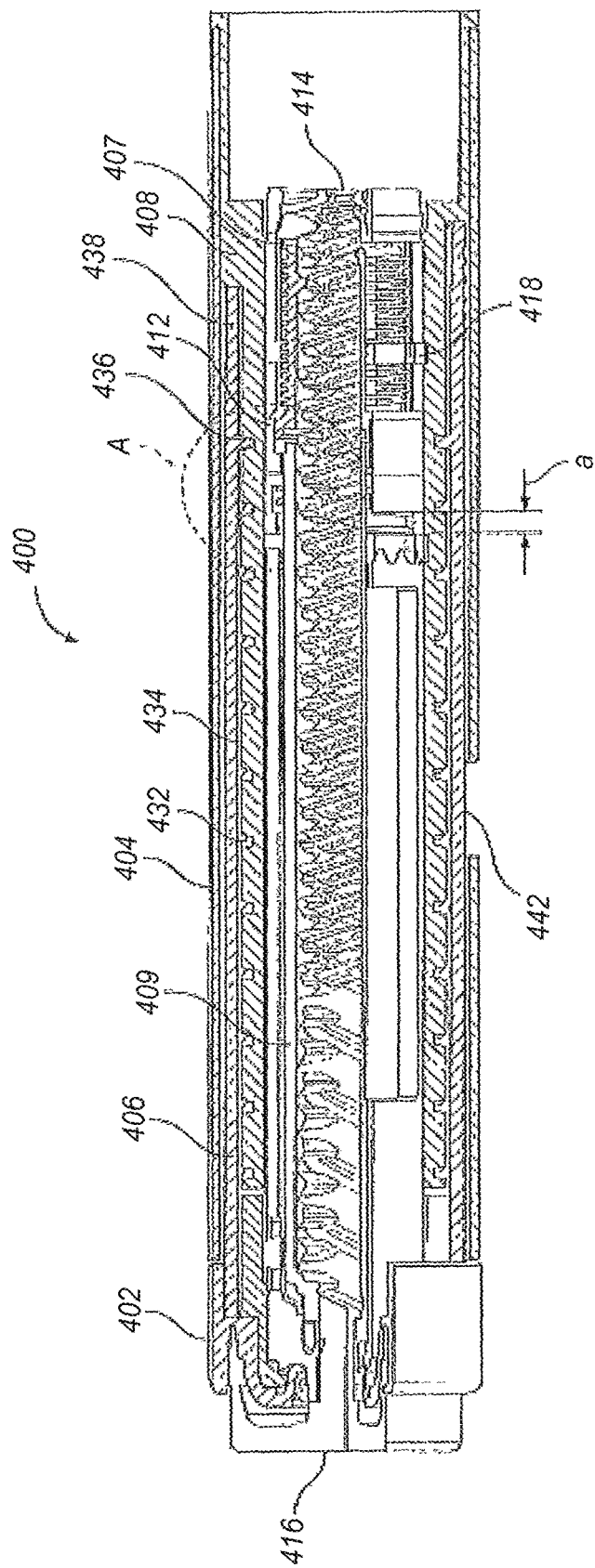
FIG. 3 shows a dose setting mechanism 400 of a drug delivery device 100 suitable for use with the invention.
Figure 4:
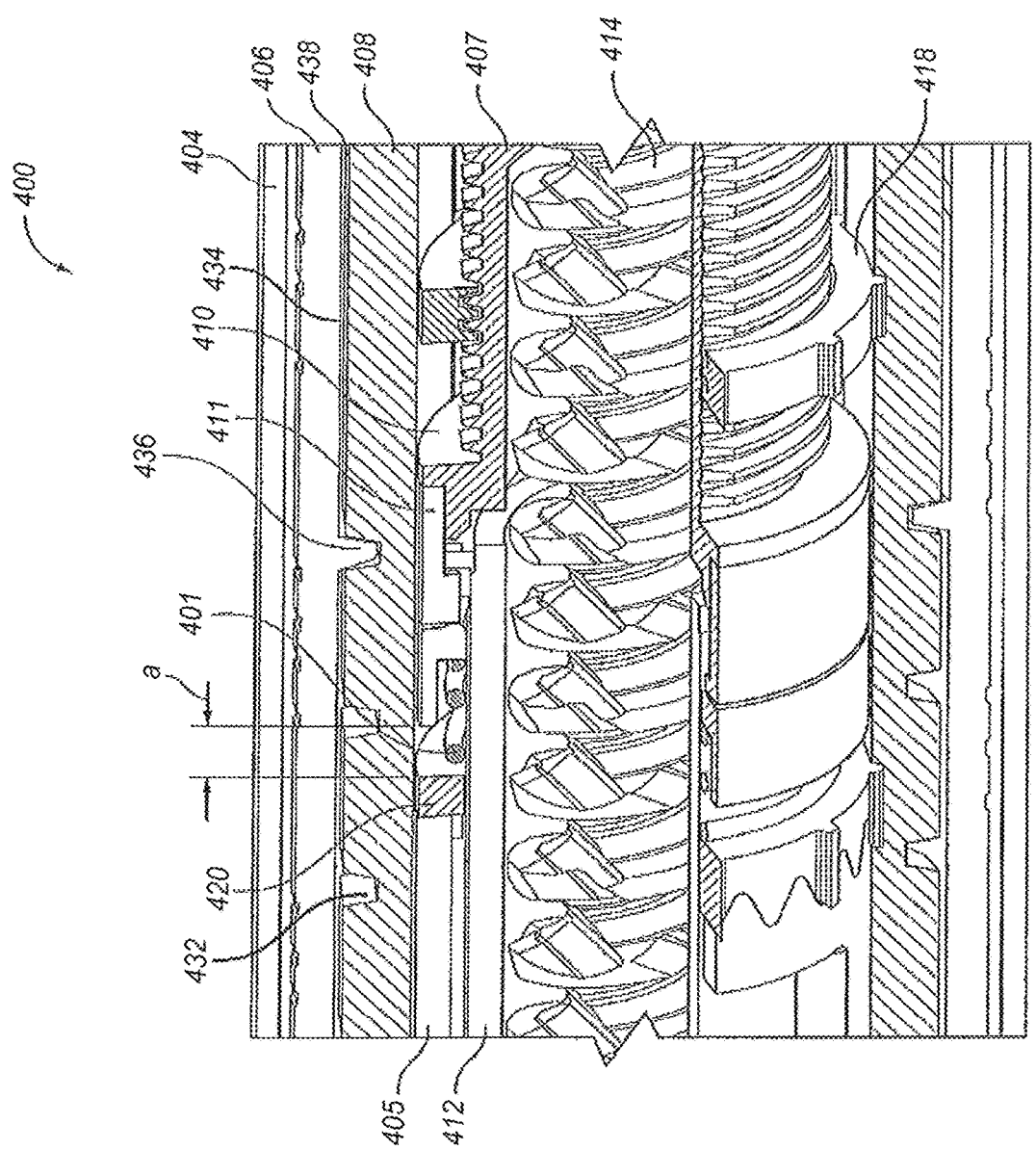
FIG. 4 shows detail of the dose setting mechanism 400 of FIG. 3.
Figure 5:
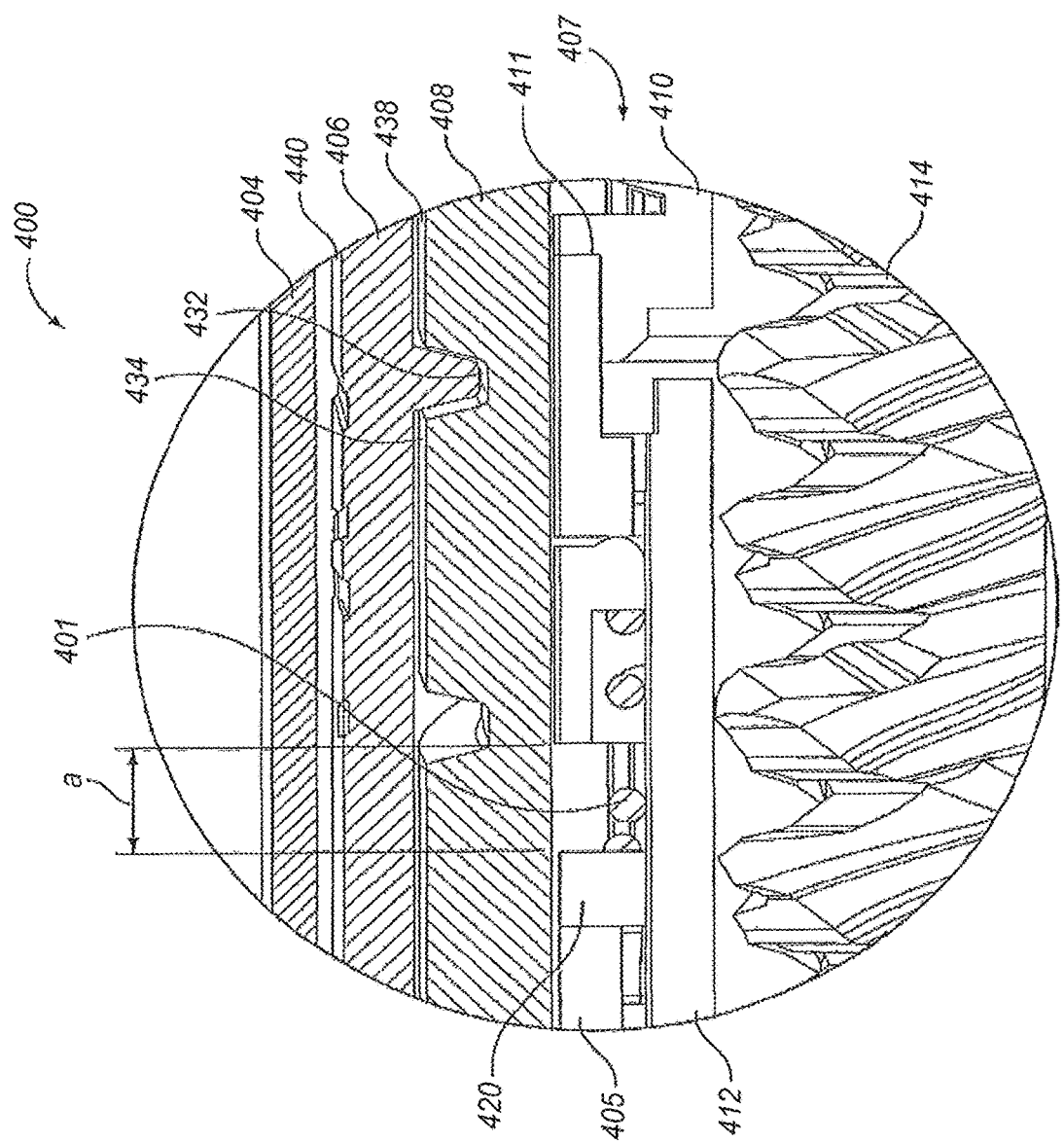
FIG. 5 shows a close up of the region marked 'A' in FIG. 3.

A fuller explanation of the operation of the dose setting and delivery mechanism supported within the first housing part 104 will now be given with reference to FIGS. 3 to 6. FIG. 3 is a cross-sectional view of a dose setting mechanism 400 of a drug delivery device 100. FIG. 4 is a detailed view of a portion of the dose setting mechanism 400. FIG. 5 illustrates a close up view of the region marked 'A' in FIG. 3.

The dose setting mechanism 400 comprises an outer housing 404, an inner housing 408 and an encoded member 406. These components are preferably hollow cylinders arranged concentrically. The encoded member 406 is disposed between the outer and inner housings 404, 408. The inner housing 408 comprises a groove 432 provided along an external surface 434 of the inner housing 408. A groove guide 436 provided on an inner surface 438 of the encoded member 406 is rotatably engaged with this groove 432. The encoded member 406 has information encoded on its outer surface 440 (see FIG. 7 for example) as will be described in more detail below.

A dose dial grip 402 is located at a proximal end of the outer housing 404. The dose dial grip 402 is disposed about an outer surface of a proximal end of the encoded member 406. An outer diameter of the dose dial grip 402 preferably corresponds to the outer diameter of the outer housing 404. The dose dial grip 402 is secured to the encoded member 406 to prevent relative movement between these two components. The dose dial grip 402 is represented in the external view of FIG. 1 by the rotatable dial 108. The dose dial grip 402 supports a dose delivery button dose delivery button 416 which has a sprung bias in a proximal direction and is configured to be depressed into the dose dial grip 402 by a user of the device 100.

A spindle 414 is disposed centrally within the mechanism 400. The spindle 414 is provisioned with at least one helical groove. In the embodiment depicted, the spindle 414 has two opposite handed overlapping groove forms that preferably extend over at least a majority of a length of the spindle. Each groove form is effectively continuous over a number of turns. In one preferred arrangement, each groove of the spindle engages either a non-continuous helical groove form on a body portion or on a driver. Preferably, either or both a non-continuous thread form on a body and a driver consists of less than one complete turn of thread. A first thread of the spindle 414 is configured to connect with a portion of the inner housing 408.

The dose setting mechanism 400 also comprises a spring 401, a clutch 405 and a driver 409 having a first driver portion 407 and a second driver portion 412. These driver portions 407, 412 extend about the spindle 414. Both the first and the second driver portions 407, 412 are generally cylindrical. The clutch 405 is disposed about the driver 409. In one arrangement, the first driver portion 407 comprises a first component part 410 and a second component part 411. Alternatively, the first driver portion 407 is an integral component part.

With the dose setting mechanism 400, as a user dials a dose with the dose dial grip 402, the metal spring 401 is selected to be strong enough to maintain engagement of both clutched couplings: the clutched coupling between the clutch 405 and the encoded member 406 and clutched coupling between the first driver portion 407 and second driver portion 412. The encoded member 406 is coupled to the dose dial grip 402 such that when a user rotates the dose dial grip 402, the encoded member 406 also rotates. As the encoded member 406 is rotated in a first rotational direction, it moves axially in a proximal direction due to its threaded connection to the inner housing 408.

When the drug delivery device is being dispensed, the user applies an axial load to the dose delivery button 416 located at the proximal end of the mechanism 400. The dose delivery button dose delivery button 416 is axially coupled to the clutch 405 and this prevents relative axial movement. Therefore, the clutch 405 moves axially towards the cartridge end or the distal end of the dose setting mechanism 400. This movement disengages the clutch 405 from the encoded member 406, allowing for relative rotation while closing up the Gap 'a'. The clutch 405 is prevented from rotating relative to a clicker 420 and hence relative to the inner housing 408. However, in this scenario, the coupling between the first driver portion 407 and the second driver portion 412 is also prevented from becoming disengaged. Therefore, any axial load on the spindle 414 only disengages the first and second driver portions 407, 412 when the dose delivery button dose delivery button 416 is not axially loaded. This therefore does not happen during dispense.

A dose limiter 418 (visible in FIG. 4) is provided on first driver portion 407 and in the illustrated arrangement comprises a nut. The dose limiter 418 has an internal helical groove matching the helical groove of the first driver portion 407. In one preferred arrangement, the outer surface of the dose limiter 418 and an internal surface of the inner housing 408 are keyed together by way of splines. This prevents relative rotation between the dose limiter 418 and the housing 408 while allowing relative longitudinal movement between these two components.

Figure 6:
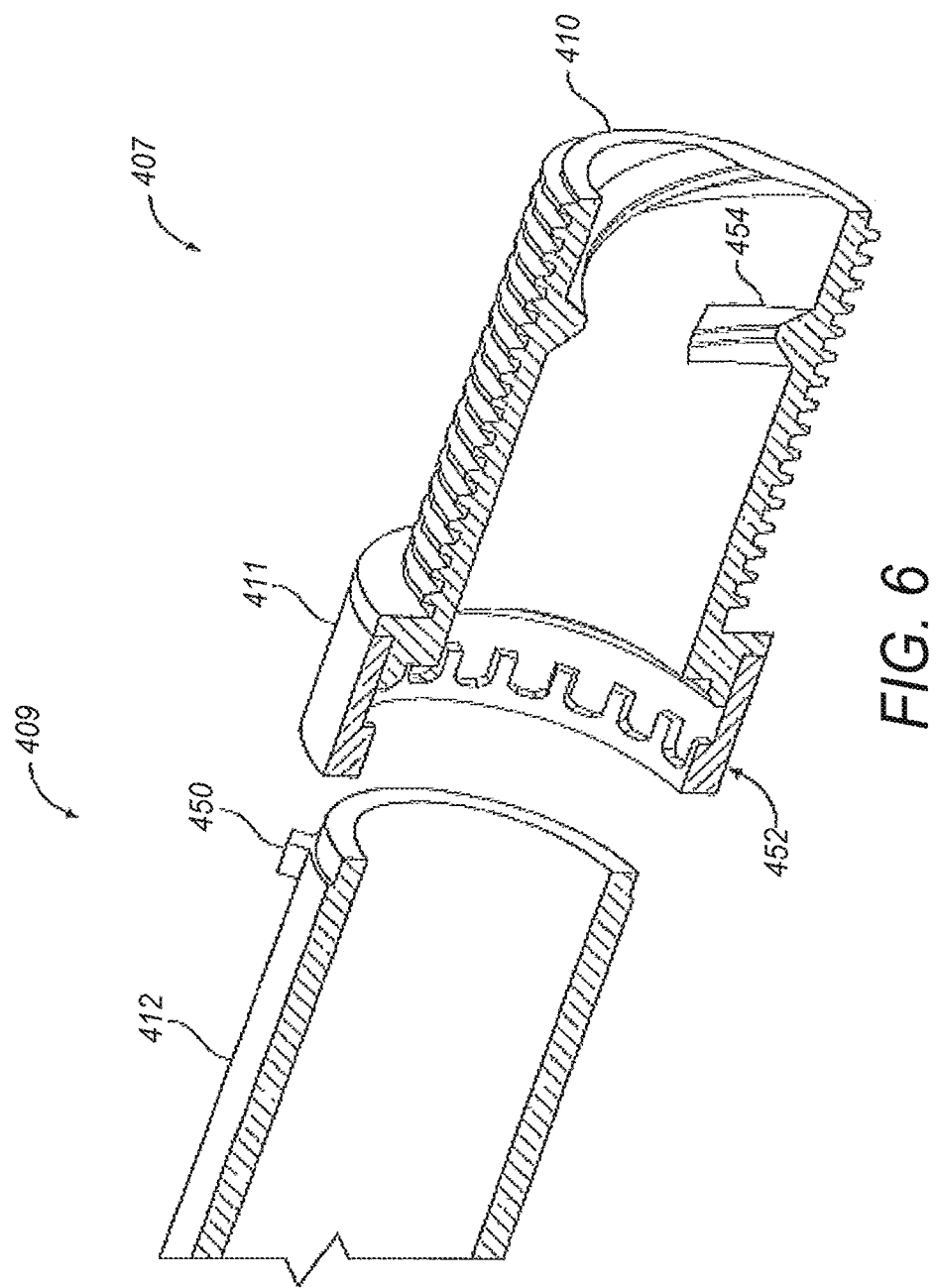
FIG. 6 is an exploded view showing details of a driver forming part of the dose setting mechanism 400 of FIGS. 3 to 5.

FIG. 6 shows in detail a first arrangement of the first driver portion 407 and the second driver portion 412 illustrated in FIGS. 3 to 5. As illustrated in FIG. 6, the second driver portion 412 is generally tubular in shape and comprises at least one drive dog 450 located at a distal end of the second driver portion 412. The first driver portion 407 also has a generally tubular shape and comprises a plurality of recesses 452 sized to engage with the drive dog 450 on the second driver portion 412. The construction of the drive dog and recesses allow disengagement with the drive dog 450 when the first and second driver portions are axially pushed together. This construction also creates a rotational coupling when these components are sprung apart.

In some embodiments, the first driver portion 407 comprises a first portion (first component part) 410 that is permanently clipped to a second portion (second component part) 411. In this arrangement, the second component part 411 comprises the plurality of recesses 452 and the first component part 410 includes the outer groove for the dose limiter 418 nut as well as an internal groove 454. This internal groove 454 is used to connect to the spindle 414 and drives the spindle 414 during dose administration. In the illustrated embodiment, the internal groove 454 comprises a part helical groove rather than a complete helical groove. One advantage of this arrangement is that it is generally easier to manufacture.

One advantage of this dose setting mechanism 400 utilizing the inner housing 408 is that the inner housing 408 can be made from an engineering plastic that minimizes friction relative to the encoded member 406 groove guide 436 and the groove 432. For example, one such engineering plastic could comprise Acetal. However, those skilled in the art will recognize that other comparable engineering plastics having a low coefficient of friction could also be used. Using such an engineering plastic enables the material for the outer housing 404 to be chosen for aesthetic or tactile reasons with no friction related requirements since the outer housing 404 does not engage any moving components during normal operation.

The effective driving diameter (represented by 'D') of the grooved interface between the encoded member 406 and the inner housing 408 is reduced compared to certain known drug delivery devices for the same outer body diameter. This improves efficiency and enables the drug delivery device to function with a lower pitch (represented by 'P') for this groove and groove guide connection. In other words, as the helix angle of the thread determines whether when pushed axially, the encoded member will rotate or lock to the inner body wherein this helix angle is proportional to the ratio of P/D.

A recess 442 in the outer housing 404 of the drug delivery device 100 can be seen in FIG. 3. This recess 442 may be configured to receive an insert or electronic module (not shown), comprising the processor 202, ROM 204, flash memory 205, RAM 206, display electronics, contacts 212 and batteries 214 previously described. Alternatively, the contacts 212 may be supported at another position on the inner surface of the outer housing 404 and linked to the processor 202 and batteries 214 by conductive paths or wires. The display mount 112 shown in FIG. 1 may be disposed on top of the insert or may be integral with the insert. The display mount 112 is configured to support the display 210. The display 210 may be larger than the recess 442 and may therefore protrude from the outer housing 404. Alternatively, both the display mount 112 and display 210 may be configured to be received by the recess 442 such that the display 210 is flush with the outer surface of the outer housing 404. The contacts 212 are configured to contact the encoded member 406 in order to facilitate a determination of the rotational position of the encoded member 406, as will be described in more detail below.

The dose setting mechanism 400 illustrated in FIGS. 3-6 is configured to be re-set to an initial position after the medicament in the attached drug cartridge has been expelled. This allows a new cartridge to be inserted and the drug delivery device 100 to be re-used. This re-setting may be achieved by pushing axially on the distal end of the spindle 414 i.e. the end which usually engages with the drug cartridge and does not require any mechanism associated with removal of a cartridge holder. As illustrated in FIGS. 3 and 4, when the first driver portion 407 is pushed axially towards the second driver portion 412 (i.e., pushed in a proximal direction) the driver 409 is decoupled from the rest of the dose setting mechanism 400.

An axial force on the spindle 414 causes the spindle 414 to rotate due to its threaded connection to the inner housing 408. This rotation and axial movement of the spindle 414 in turn causes the first driver portion 407 to move axially towards the second driver portion 412. This will eventually decouple the first driver portion 407 and second driver portion 412.

This axial movement of the first driver portion 407 towards the second driver portion 412 results in certain advantages. For example, one advantage is that the metal spring 401 will compress and will therefore close the Gap 'a' illustrated in FIGS. 3-5. This in turn prevents the clutch 405 from disengaging from the clicker 420 or from the encoded member 406. The second driver portion 412 is prevented from rotation since it is splined to the clutch 405. The clicker 420 is splined to the inner housing 408. Therefore, when the Gap 'a' is reduced or closed up, the second driver portion 412 cannot rotate relative to either the inner housing 408 or the encoded member 406. As a consequence, the encoded member 406 cannot rotate relative to the inner housing 404. If the encoded member 406 is prevented from rotating then, as the spindle 414 is retracted back into the dose setting mechanism 400 and thereby re-set, there will be no risk of the encoded member 406 being pushed out of the proximal side of the dose setting mechanism 400 as a result of a force being applied on the spindle 414.

Another advantage of a dose setting mechanism 400 comprising an inner housing 408 is that the dose setting mechanism 400 can be designed, with a slight modification, as a drug delivery device platform that is now capable of supporting both re-settable and non-resettable drug delivery devices. As just one example, to modify the re-settable dose setting mechanism 400 variant illustrated in FIGS. 3-6 into a non-resettable drug delivery device, the first component part 410 and the second component part 411 of the first driver portion 407 and the second driver portion 412 can be moulded as one unitary part. This reduces the total number of drug delivery device components by two. Otherwise, the drug delivery device illustrated in FIGS. 3-6 could remain unchanged. In such a disposable device, the second housing part 106 would be fixed to the first housing part 104 or alternatively made as a single one piece body and cartridge holder.

The dose setting mechanism described above is merely one example of a mechanism suitable for supporting the encoded member 406 and for implementing the present invention. It will be apparent to the skilled person that other mechanisms may also be suitable. For example, a mechanism which does not include an inner housing 408, but in which the encoded member 406 is still visible to the sensor 112 would be equally suitable.

First Embodiment

In view of the foregoing it will be appreciated that a user twists the rotatable dial 108 to select an amount of dose to be dispensed from a drug cartridge. This causes the encoded member 406 to rotate and translate axially (longitudinally) relative to the housing 102. By analysing information provided on the outer surface 440 of the encoded member 406 the extent of rotation of the dial 108, and thus the amount of dose dialled, can be determined. Furthermore, a user presses the dose delivery button 416 to dispense an amount of dose from within a drug cartridge. Pressing the dose delivery button 416 causes the encoded member 406 to rotate and move axially the other way. Thus by analysing information provided on the outer surface 440 of the encoded member 406 how far the encoded member 406 has been translated within the housing, and thus the amount of dose dispensed, can also be determined.

Figure 7:
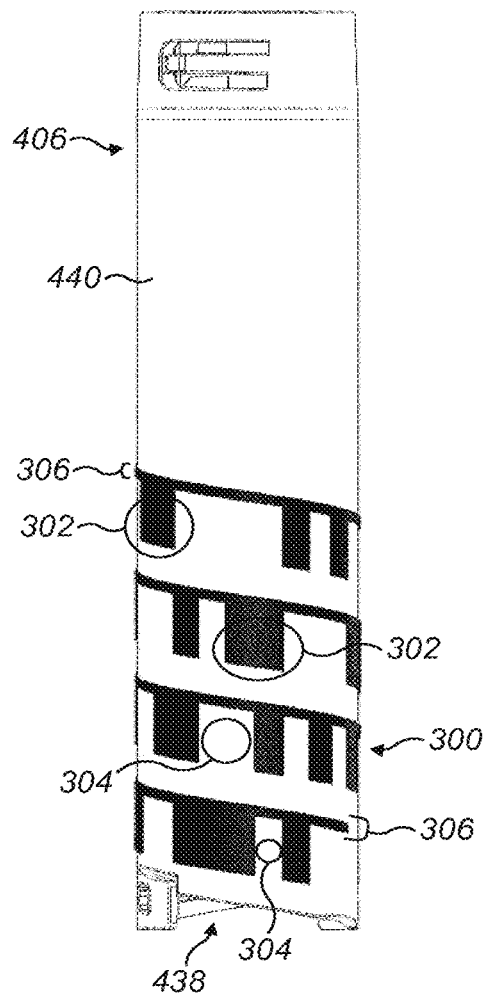
FIG. 7 shows an encoded member 406 according to a first embodiment of the present invention.

FIG. 7 illustrates an encoded member 406 according to a first embodiment of the present invention. The encoded member 406 is a hollow cylinder or sleeve having an outer surface 440 and an inner surface 438. The outer surface 440 comprises a helical track 300 forming an encoder. FIG. 7 shows that the helical track comprises a series of conductive segments 302 (shown in black) that are electrically coupled to one another by a power line 306 (also shown in black). Non-conductive or insulating segments 304 (shown in white) are defined in the space between respective conductive segments 302.

Figure 8:
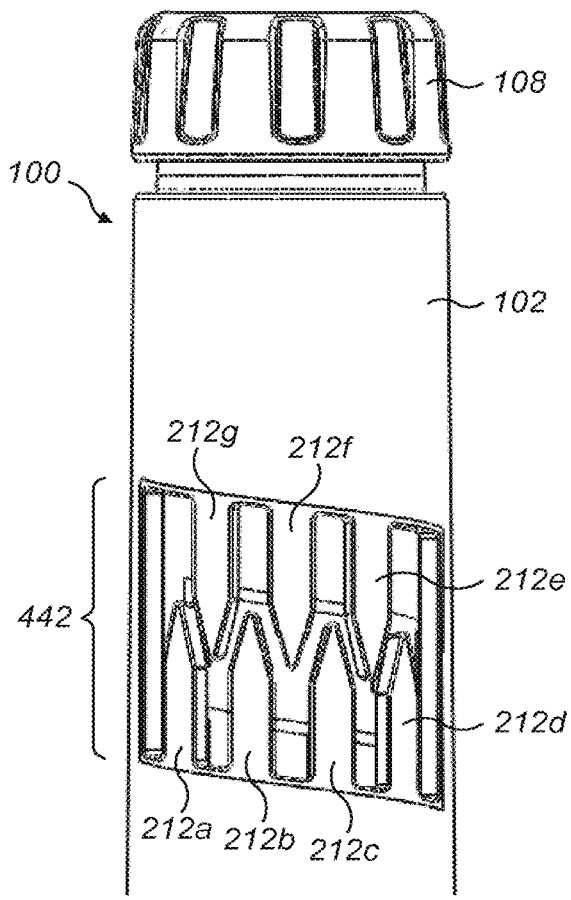
FIG. 8 shows an external view of part of a drug delivery device 100 according to a first embodiment of the present invention.

A drug delivery device 100, according to a first embodiment thereof, is provided with contacts 212a-212g that engage the helical track 300 at different locations along the length of the track 300 as depicted in FIG. 8. It should be remembered that when the encoded member 406 is caused to rotate, the encoded member 406 moves axially within the housing 102. Since the contacts 212a-212g are fixed in position relative to the housing 102, rotating the encoded member 406 causes respective conductive and non-conductive segments 302, 304 of the helical track 300 to sweep across the contacts 212a-212g.

The processor 202 is capable of determining the extent of rotation of the encoded member 406 (and thus how far it has travelled axially) by analysing which contacts 212a-212g engage conductive segments 302 and which contacts engage non-conductive segments 304. How this is achieved will be explained in more detail below after the configuration of the encoded member 406 has been set out in more detail Referring back to FIG. 7, the inner surface 438 of the encoded member 406 may have a helical thread (shown as inner groove 436 in FIGS. 3 to 5). This thread 436 may extend over a single turn or over a partial turn. Alternatively, this thread 436 may comprise several turns. The encoded member 406 may be made of a plastic material. The encoded member 406 is configured to be incorporated into the drug delivery device 100 as shown in FIGS. 3 to 5. The inclusion of an inner housing 408 enables the encoded member 406 to have a helical thread 436 on the inner surface 438 rather then the outer surface 440. This results in a number of advantages. For example, this results in the advantage of providing more surface area along the outer surface 440 of the encoded member 406 for the helical track 300. Another advantage is that this inner groove 436 is now protected from dirt ingress. In other words, it is more difficult for dirt to become lodged in this inner groove interface than if the groove were provided along the outer surface 440 of the encoded member 406. This feature is particularly important for a re-settable drug delivery device which is required to function over a much longer period of time compared to a non-resettable device.

The helical track 300 may be formed on the outer surface 440 of the encoded member 406 by wrapping a metallic strip around the encoded member 406. Such a metallic strip may have a non-conductive backing to support the metallic layer. The non-conductive backing may have an adhesive on the reverse side for securing the strip to the outer surface 440 of the encoded member 406. The helical track 300 may alternatively comprise conductive ink printed onto a non-conductive substrate. This non-conductive substrate may be the encoded member 406 itself or a secondary substrate which is subsequently attached to the encoded member 406.

Figure 9:
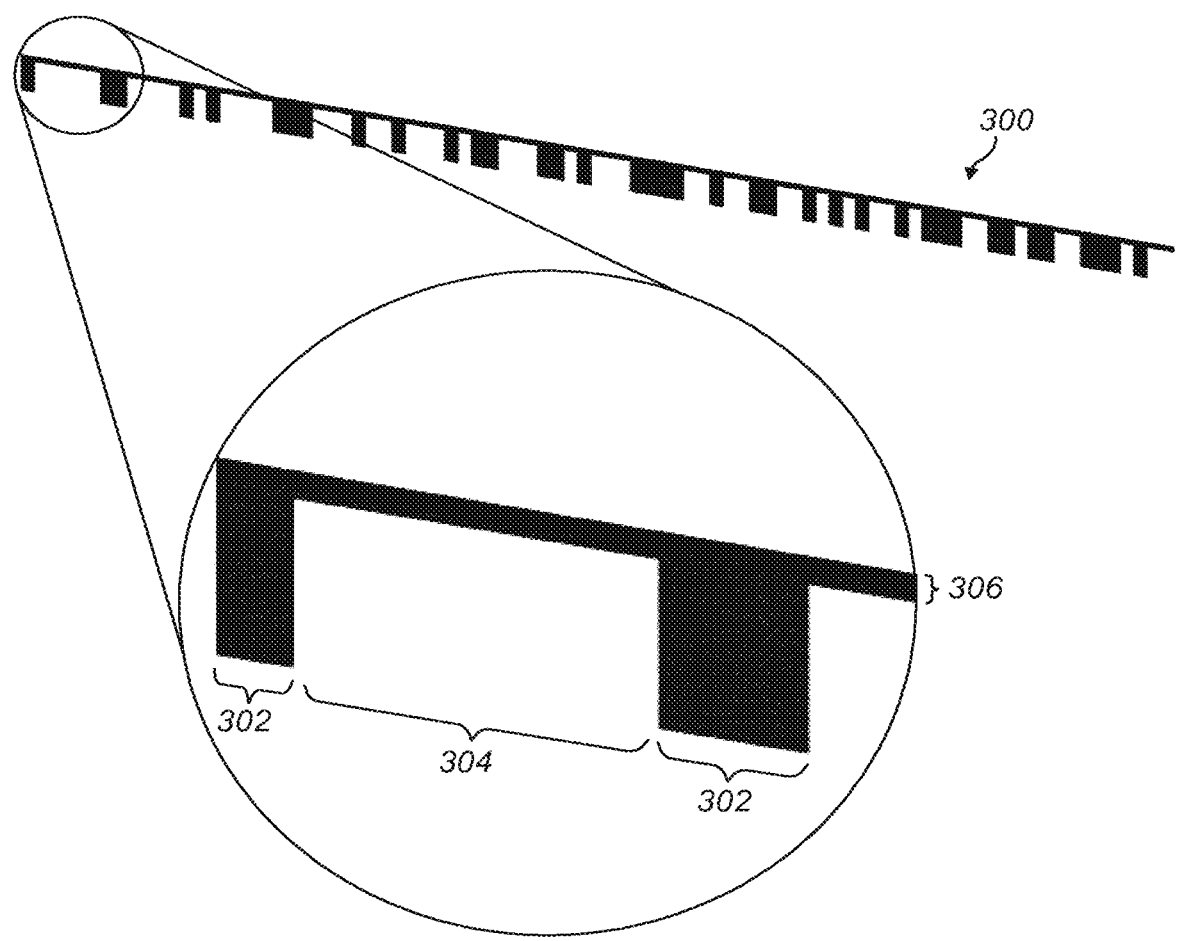
FIG. 9 shows a coded strip 300 suitable for use in manufacturing the encoded member 406 in FIG. 7.

FIG. 9 illustrates the helical track 300 (which, as mentioned could be a metallic strip) in unwrapped form. Part of the track 300 in FIG. 9 is shown as being magnified. The conductive segments 302 (shown in black) are electrically coupled to one another via a power line 306 (also shown in black). It will therefore be appreciated that applying a voltage to one of the conductive segments 302 causes all of the conductive segments 302 to be energised by virtue of their electrical connection to the power line 306.

Preferably seven contacts 212a-212g are arranged around the encoded member 406, as depicted in FIG. 8. The contacts 212a-212g are arranged so as to engage the encoded member 406 at different locations along the length of the helical track 300 (note that the seven contacts 212a-212g do not engage the power line 306 and may only engage the conductive and non-conductive segments 302, 304 of the helical track 300). The contacts 212a-212g may be angularly separated by 15 degrees relative to one another along the length of the helical track 300. The pitch of the helix along which the contacts 212a-212g are formed is the same as the pitch of the helix of the helical track 300, which is the same as the pitch of the threads that constrain movement of the encoded member 406 relative to the inner housing 408.

Displacing the contacts 212a-212g along the length of the helical track 300 provides that, for a given rotational position of the encoded member 406, some of the contacts 212a-212g engage conductive segments 302 whereas the other contacts engage non-conductive segments 304. The helical track 300 shown in the drawings is configured such that for each rotational position of the encoded member 406, at least two contacts 212a-212g are in engagement with conductive segments 302.

Looking again at FIG. 8 the contacts 212a-212g are shown supported in the recess 442 (the display mount 112 not being shown). The contacts 212a-212g may be biased against the outer surface 440 of the encoded member 406 in order to provide a stable electrical connection with the helical track 300. Additionally, the contacts 212a-212g are inclined relative to the longitudinal axis of the device 100 by the same degree as the pitch of the helical track 300. The pitch of the helical track 300 is the same as the pitch of the groove guide 436 of the encoded member 406 which engages with the inner housing groove 432. Therefore, when the encoded member 406 rotates and moves axially within the housing 102, the helical track 300 is always positioned directly underneath the contacts 212a-212g. More specifically the section of helical track 300 comprising the conductive and non-conductive segments 302, 304 is always positioned directly underneath the contacts 212a-212g. As previously mentioned, the contacts 212a-212g do not engage the power line section 306 of the helical track 300.

How the processor 202 is able to determine the extent of rotation of the encoded member 406 (and thus how far it moves axially) will now be explained. The processor 202 is configured to address each of the contacts 212a-212g individually. The processor 202 is also configured to control the provision of a voltage signal from the batteries 214 to each contact. However, when the batteries 214 provide a signal having a voltage to one of the contacts 212a-212g, certain others of the contacts may also be energised by virtue of being in electrical connection with the first contact via the power line 306. Thus, the batteries may provide a voltage to a first of the contacts (for example, contact 212a) and the processor 202 may detect signals from each of the other contacts that are energised due to being in electrical connection with the first contact 212a through the power line 306. Since the processor 202 can address the contacts 212a-212g individually, it is able to apply a signal to different contacts, each time monitoring signals from the other contacts.

It may be that the drug delivery device 100 shown in FIG. 1 is an insulin pen type injection device. Users may need to set an insulin dose of between 1 and 80 International Units. Advantageously, the helical track 300 utilised in conjunction with seven contacts 212a-212g provides a seven bit encoding system. This allows $2^7=128$ discrete rotational positions of the encoded member 406 to be uniquely encoded. Thus the full 0-80 unit dial-able dose for an injection device can be absolutely encoded with redundant positions available.

The seven bit encoding system is realised by arranging the foregoing conductive and non-conductive segments 302, 304 of the helical track 300 such that they form a type of code. FIG. 10 illustrates how the seven contacts 212a-212g of the present embodiment (depicted as contacts 1-7) move into and out of engagement with conductive and non-conductive segments 302, 304 of the helical track 300 when the encoded member 406 is moved rotationally (and thus axially) relative to the housing 102.

A code digit of "1" denotes that a contact engages a conductive segment 302 whereas a code digit of "0" denotes that a contact engages a non-conductive segment 304. From FIG. 10 it will be apparent that when the seven contacts 212a-212g move along the helical track 300 (upon rotation and thus axial movement of the encoded member 406) the contacts come into engagement with various unique configurations of conductive and non-conductive segments 302, 304. In particular, in the illustrative example of the present embodiment, the contacts encounter 81 unique configurations of conductive and non-conductive segments 302, 304 as they move along the helical track 300.

FIG. 11 depicts a numerical representation of the track 300 in FIG. 9. From FIG. 11 the 81 unique seven bit binary codes associated with the 81 unique rotational positions of the encoded member 406 can be determined.

When a user of the device 100 twists the rotatable dial 108 (see FIG. 8) to select or dial in a drug dose, the processor 202 may be activated and may be controlled by software stored in the ROM 204 to execute a check on the contacts 212a-212g to determine the absolute rotational position of the encoded member 406, and hence the drug dose which has been dialled. The processor 202 may also be configured to determine the number of drug units which have been delivered.

The process of determining a dialled dose will now be described. In order to determine the drug dose which has been dialled, the processor 202 first causes the batteries 214 to apply a voltage to a first contact (for example, contact 212a) and then the processor determines which of the remaining six contacts are energised. It should be remembered that in the present embodiment, for each rotational position of the encoded member 406 at least two contacts 212a-212g engage a conductive segment 302 of the helical track 300. Thus when a voltage is applied to the first contact 212a, if any of the remaining six contacts 212b-212g are energised then both the first contact and the other energised contacts are associated with a code value of "1". This denotes that such contacts are in engagement with a conductive segment 302 of the track 300. The contacts that were not energised are associated with a code value of "0". This denotes that such contacts are in engagement with a non-conductive segment 302 of the track 300.

Analysing which contacts are associated with a code value of "1" and which are associated with a code value of "0", the processor 202 can determine the unique seven bit binary code associated with the absolute rotational position of the encoded member 406. The processor 202 can then use the seven bit binary code to determine the dialled drug dose. This may be achieved by the processor 202 upon searching a lookup table stored in the ROM 204, the lookup table providing a conversion from the seven bit binary code result to a dose unit dialled.

If however, when a voltage is applied to the first contact (for example contact 212a) none of the other contacts 212b-212g are determined to be energised then the processor 202 instead applies a voltage to another one of the contacts (for example, the second contact 212b). The processor then determines whether any of the other contacts are energised upon applying a voltage to the second contact 212b. This process is repeated for respective contacts until at least one of the seven contacts 212a-212g is detected as being energised upon application of a voltage to another one of those contacts. When this is detected as taking place the processor 202 uses the seven bit binary code associated with the absolute rotational position of the encoded member 406 to determine the dialled dose in the manner heretofore described. In particular the processor 202 compares the seven bit binary code with a lookup table to determine the dialled dose amount.

As an illustrative example, before dialling a dose by twisting the rotatable dial 108 the encoded member 406 may be in a position associated with the code depicted on the left-hand side in FIG. 10. In such a "0" position (i.e. the zero dose dialled position) the processor 202 will detect the seventh contact 212g to be energised when a voltage is applied to the first contact 212a. This is because in position "0" only the first and seventh contacts 212a, 212g engage conductive segments 302 of the helical track 300, whereas the other contacts 212b-212f engage non-conductive segments 304. In effect the binary result "1000001" is read by the processor 202. From this the device 100 is determined by the processor 202 to be in the zero dose dialled configuration upon consulting a lookup table. This is because in such a lookup table a dialled dose amount of "zero dose units" will be associated with the binary code value "1000001". It is envisaged that a dialled dose amount of zero may be shown on the display 210 to a user of the drug delivery device 100.

Upon dialling a dose by twisting the rotatable dial 108 the encoded member 406 may be moved into a position associated with the code depicted on the right-hand side in FIG. 10 denoted as position "2". In this configuration no additional contacts will be determined by the processor 202 to be energised when a voltage is applied to any of contacts one to four 212a-212d. However, upon applying a voltage to the fifth contact 212e the processor 202 will detect contact six 212f as being energised. This is because in position "2" only the fifth and sixth contacts 212e, 212f engage conductive segments 302 of the helical track 306. In effect the binary code "0000110" will be read by the processor 202. From this the processor 202 can determine that Y dose units have been dialled upon consulting the aforementioned lookup table. This is because in such a lookup table a dialled dose amount of Y dose units will be associated with binary code value "0000110". It is envisaged that a dialled dose amount of Y dose units may be shown on the display 210 to a user of the drug delivery device 100.

It will be appreciated that in other arrangements the code defined by the helical track 300 may have a different configuration, in particular it may define a different combination of "0"s and "1"s to that used in the above illustrative example.

In addition to (or instead of) determining a dialled dose, the device 100 may be configured to determine an amount of dose that has been dispensed. For example, when an amount of dose has been dispensed the processor 202 may determine the position of the encoded member 406 relative to the housing 102 in the foregoing manner. In particular the processor 202 may determine the seven bit binary code associated with the absolute rotational position of the encoded member 406. The dose amount associated with such a binary code may then be determined from a lookup table. The processor 202 may determine the drug dose which has been dispensed (or is yet to be dispensed, if any) by subtracting a remaining drug dose from an initially dialled drug dose. It is envisaged that the display 210 may be used to show the dose amount yet to be dispensed if a user does not dispense the full amount of a dialled dose.

Having determined the drug dose which has been dispensed, the processor 202 may store the result in the flash memory 205. As mentioned above the display 210 may be controlled to display the result of the dispensed dose determination. The display 210 may show the result of the dispensed dose determination for a predetermined time, for example 60 seconds. Alternatively or in addition, the dispensed dose history may be retrieved electronically from the flash memory 205 by a user of the device 100 or by a health care professional. During dialling of the device, the dialled dose may be indicated to the user in any conventional way, for example by use of numerals printed on the encoded member. In some other embodiments, the dialled dose is not determined or indicated to the user.

Although a seven bit coding system has been described, the first embodiment is equally applicable for any number of contacts greater than three, in other words at least contacts 212a-212d. The seven bit system is preferred as it allows the full 0-80 unit dose range to be absolutely encoded.

Furthermore, the processor 202 may implement the process of checking the contacts 212a-212g while the encoded member 406 is actually rotating, i.e. while the device 100 is actually being dialled or is being used to dispense a substance. Alternatively the checking process may only be performed when the processor 202 detects that the encoded member 406 has been in a certain position for a predetermined amount of time (for example 100 milliseconds), thereby indicating that the device 100 has been dialled or dispensed an intended amount by a user.

Second Embodiment

Figure 12:
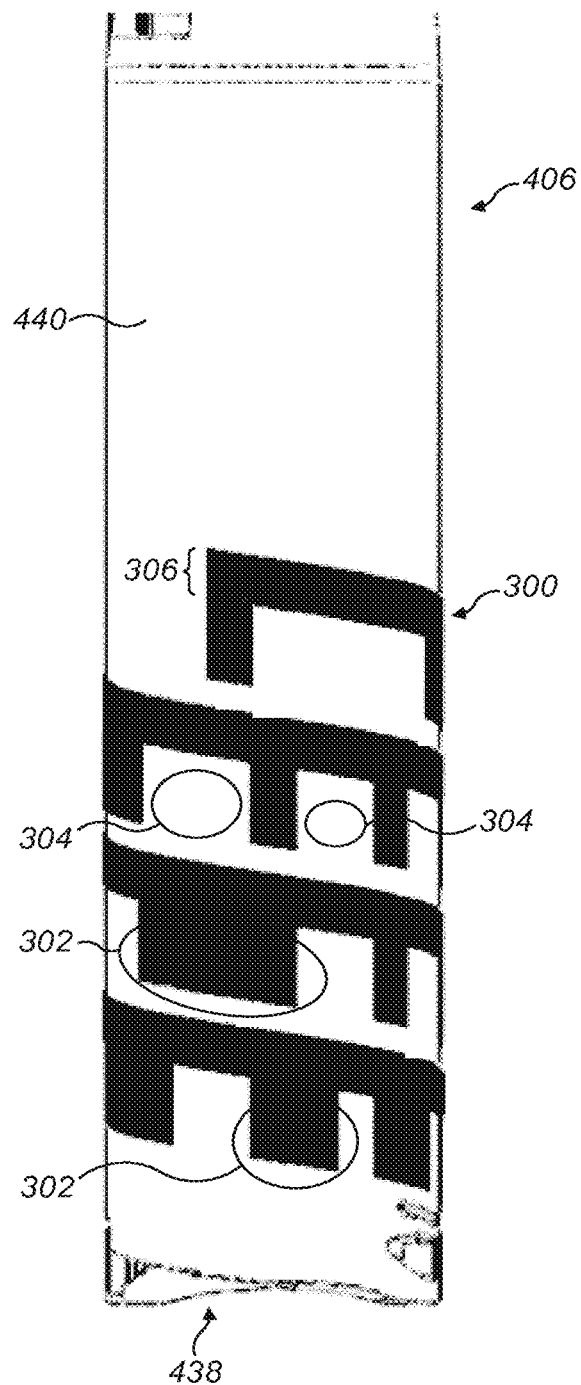
FIG. 12 shows an encoded member 406 according to a second embodiment of the present invention.

FIG. 12 illustrates an encoded member 406 according to a second envisaged embodiment of the present invention. This encoded member 406 differs from the embodiment shown in FIG. 7 in that the power line 306 is slightly thicker, i.e. has a greater dimension in the axial direction, in the present embodiment. In particular the power line 306 depicted in FIG. 12 is thick enough to accommodate an additional, eighth electrical contact 212h.

Figure 13:
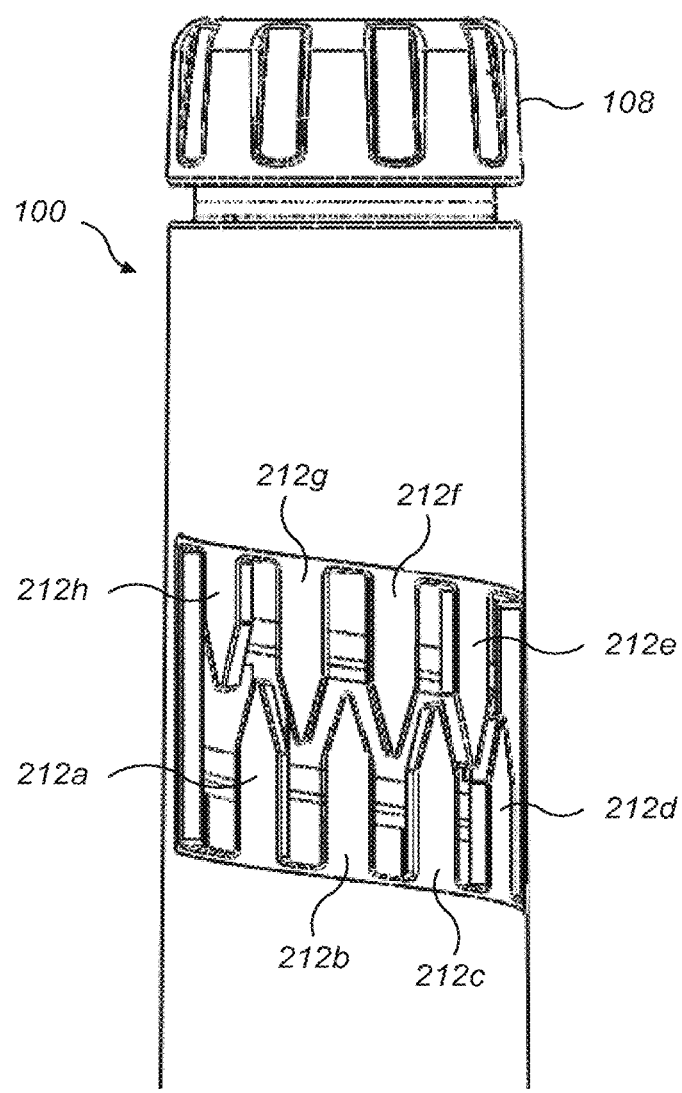
FIG. 13 shows an external view of part of a drug delivery device 100 according to a second embodiment of the present invention.

FIG. 13 shows part of a drug delivery device 100 according to a second embodiment thereof, the device 100 having an additional, eighth, contact 212h (the display mount 112 not being shown). The other seven electrical contacts 212a-212g are similar to those previously described in connection with FIG. 8 and, as in the previous embodiment, are configured to engage the conductive and non-conductive segments 302, 304 of the helical track 300. In the present embodiment however the helical track 300 and the contacts 212a-212g are arranged such that in each rotational position of the encoded member 406 at least one (rather than at least two) of the seven contacts 212a-212g engage a conductive segment 302 of the helical track 300.

The eighth contact 212h is arranged to remain in contact with the thicker power line 306 when the encoded member 406 rotates and moves axially relative to the housing (i.e. when a dose is being dialled or dispensed). As such, the eighth contact 212h will be referred to hereafter as the power line contact 212h.

In this embodiment of the drug delivery device 100 the processor 202 is configured to cause the batteries 214 to continually apply a voltage to the power line contact 212h when determining the absolute rotational position of the encoded member 406, and therefore an amount of dose dialled or dispensed. Furthermore, in the present embodiment the helical track 300 and the contacts 212a-212g are arranged such that when a voltage is applied to the power line contact 212h at least one of the seven contacts 212a-212g is energised.

Since the conductive segments 302 of the helical track 300 are electrically coupled to one another via the power line 306, when a voltage is applied to the power line contact 212*h* the other seven contacts 212*a*-212*g* are energised whenever they engage a conductive segment 302 of the helical track 300. This enables the processor 202 to determine the absolute rotational position of the encoded member 406 in a different way to that previously described. In particular, the algorithm of applying voltages to respective contacts 212*a*-212*g* one-by-one until at least one other contact is detected to be energised is not necessary. Instead, applying a continuous voltage to the power line 306 (via the power line contact 212*h*) causes all contacts 212*a*-212*g* in engagement with conductive segments 302 of the helical track 300 to be energised. Therefore the processor 202 can determine the absolute rotational position of the encoded member 406 by directly analysing which contacts 212*a*-212*g* are energised when the power line contact 212*h* is switched on.

For instance when a user of the drug delivery device 100 twists the rotatable dial 108 to set a drug dose (see FIG. 13), the processor 202 may be activated and controlled by software stored in the ROM 204 to cause the batteries 214 to apply a voltage to the power line contact 212*h*. The processor 202 may also be controlled by the software to execute a check on the other seven contacts 212*a*-212*g* to determine which of them have been energised. This enables the seven bit binary code associated with the absolute rotational position of the encoded member 406 to be directly determined by the processor 202. Comparing this binary code with a lookup table in the manner heretofore described enables the amount of dose dialled to be determined.

Similarly an amount of dose that has been dispensed may be determined in a corresponding way. In particular when a dose amount has been dispensed the processor 202 may directly determine which of the seven contacts 212*a*-212*g* are energised upon causing the batteries 214 to apply a voltage to the power line contact 212*h*. From this the seven bit binary code associated with the absolute rotational position of the encoded member 406 may be assembled and compared with a lookup table in order to determine a dose amount associated with that absolute rotational position. From this the processor 202 may then calculate the dose which has been dispensed (or is yet to be dispensed, if any) by subtracting a remaining dose amount from an initially dialled dose.

Further envisaged arrangements of the second embodiment described herein will now be briefly outlined.

Although a seven bit system has been described, the second embodiment is equally applicable for any number of position determining contacts greater than three, in other words at least contacts 212*a*-212*d* shown in FIG. 13. This is of course in addition to the power line contact 212*h*. The seven bit system is advantageous as it allows the full 0-80 unit dose range to be absolutely encoded.

The processor 202 may implement the process of checking the contacts 212*a*-212*g*, upon application of a voltage to the power line contact 212*h*, while the encoded member 406 is actually rotating i.e. while the device 100 is being dialled or is being used to dispense a dose. Alternatively the checking process may only be performed when the processor 202 detects that the encoded member 406 has been in a certain position for a predetermined amount of time (for example 100 milliseconds), thereby indicating that the device has been dialled or dispensed an intended amount by a user.

Furthermore, the code defined by the helical track 300 may have a different configuration, in particular it may define a different combination of "0"s and "1"s to the code shown in FIG. 12. It is envisaged that the conductive and non-conductive segments 302, 304 may be arranged relative to the contacts 212*a*-212*g* to define a Gray code or a reflected binary code.

Third Embodiment

Figures 14A, 14B:
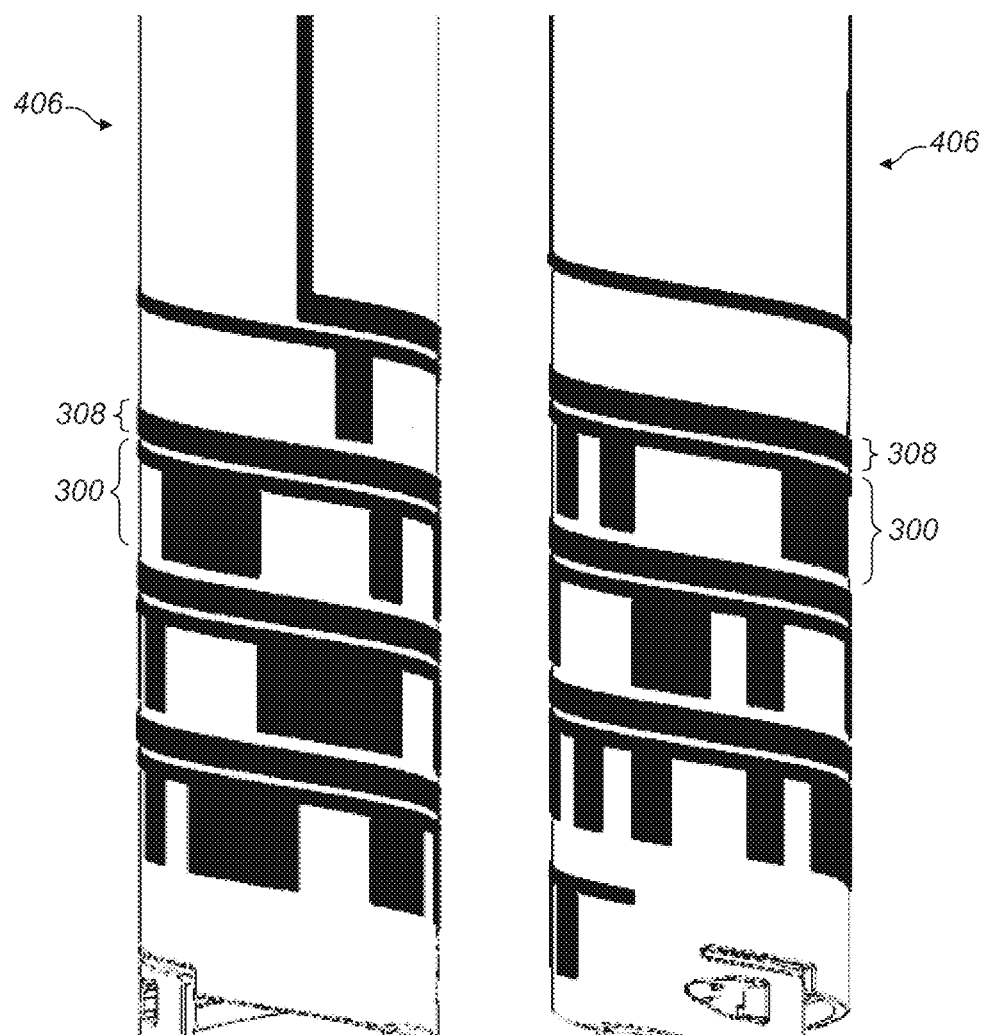
FIGS. 14a and 14b respectively show front and rear views of an encoded member 406 according to a third embodiment of the present invention.

FIGS. 14*a* & 14*b* illustrate front and reverse views of an encoded member 406 according to a third embodiment of the present invention. This encoded member 406 differs from the embodiment shown in FIG. 7 in that an additional track 308 is provided on the outer surface 440 adjacent the helical track 300 which forms an encoder. As such, the helical track 300 will be referred to hereafter as the first helical track 300 and the additional track 308 will be referred to hereafter as the second helical track 308.

Figure 15:
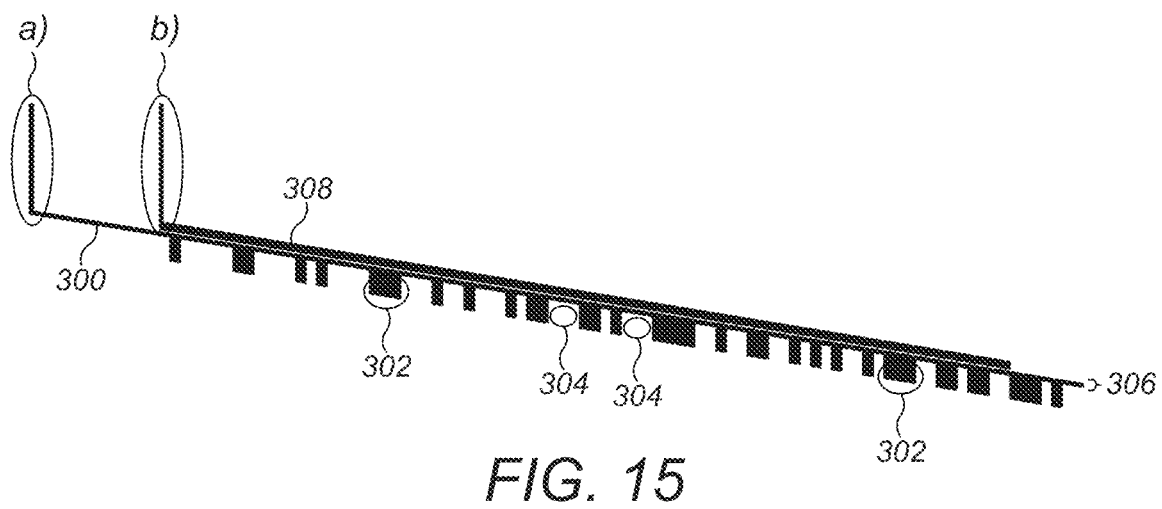
FIG. 15 shows a coded strip 300 and an additional strip 308 suitable for use in manufacturing the encoded member 406 in FIGS. 14a and 14b.

FIG. 15 shows these two tracks in unwrapped form and it will be appreciated that the second helical 308 track essentially comprises a continuous electrically conductive member. The pitch of the second helical track 308 is the same as the pitch of the first helical track 300. Also, the distance between the two helical tracks and the sections labelled a) and b) in FIG. 15 may be varied, for example they may be greater or smaller provided that the separate helical tracks 300, 308 do not electrically connect with one another. In one particular arrangement the sections labelled a) and b) in FIG. 15 may be set at half the circumference of the encoded member's outer surface 440.

Figure 16:
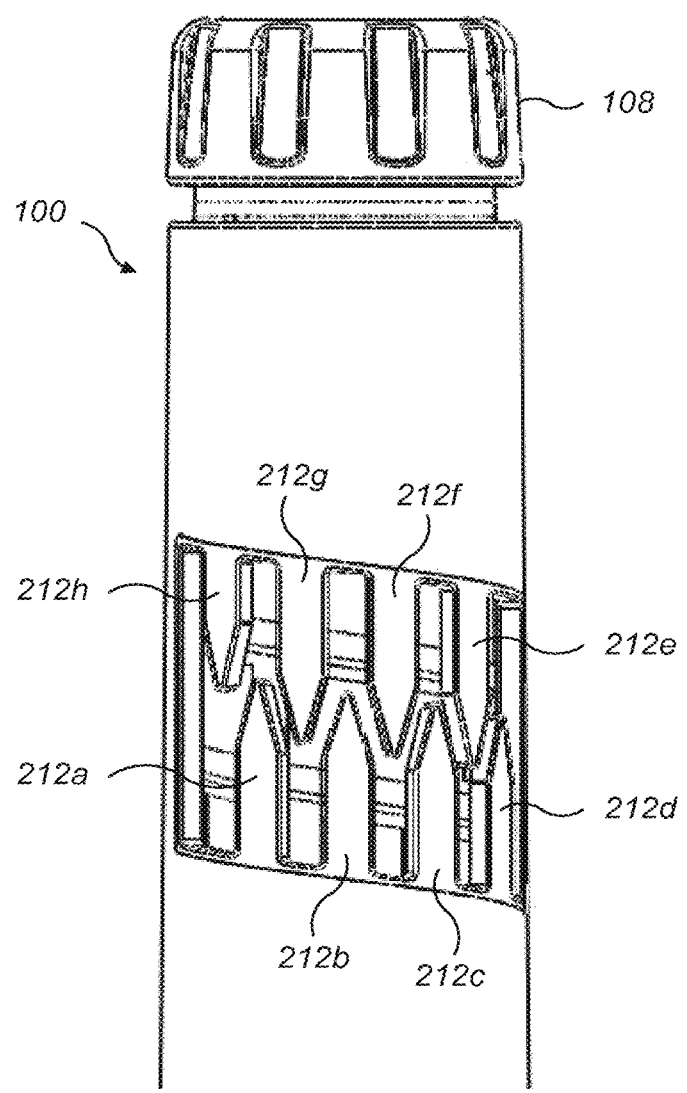
FIG. 16 shows an external view of part of a drug delivery device 100 according to a third embodiment of the present invention.

A drug delivery device 100, according to a third embodiment thereof, is provided with an additional, eighth, contact 212*i*. FIG. 16 (in which the display mount 112 is not shown) depicts such an additional contact 212*i*, wherein contacts 212*a*-212*g* are the same as those illustrated in FIG. 8. As such, the seven contacts 212*a*-212*g* engage conductive and non-conductive segments 302, 304 of the first helical track 300 during rotation of the encoded member 406. The additional, eighth, contact 212*i* is arranged to remain in contact with the second helical track 308 when the encoded member 406 rotates and moves axially relative to the housing (i.e. when a dose is being dialled or dispensed). For reasons which will become apparent later the eighth contact 212*i* will be referred to hereafter as the mode-shift contact 212*i*.

An electrical conduction path (not shown) may join the first and second helical tracks 300, 308. The switch 216 (see FIG. 2) is disposed in this electrical conduction path. The switch 216 is configured to connect electrically the first and second helical tracks 300, 308 when the device 100 is idle or when a drug dose is being set by rotation of the rotatable dial 108 (see FIG. 16). This allows the processor 202 to determine that the device 100 is in dialling mode. The switch 216 is also configured to isolate electrically, or disconnect, the first and second helical tracks 300, 308 when a drug dose is being delivered. This allows the processor 202 to determine that the device 100 is in dispensing mode.

In particular the switch 216 may be coupled to the dose delivery button 416 (see FIG. 3) supported by the rotatable dial 108, such that when the button is depressed, the switch 216 disconnects the first and second helical tracks 300, 308.

When a drug delivery device 100 according to the present embodiment is in use the processor 202 determines the absolute rotational position of the encoded member 406 in the manner heretofore described in connection with the first embodiment shown in FIG. 7. In particular the processor 202 is activated and controlled by software stored in the ROM 204 to execute a check on the contacts 212*a*-212*g* shown in FIG. 16 to determine the seven bit binary code associated with the absolute rotational position of the encoded member 406. In the present embodiment however the processor 202 is additionally configured to determine the status of the switch 216 and hence whether the device 100 is in dialling or dispensing mode.

The process of determining a dialled dose will now be described. When a user twists the rotatable dial 108 (see FIG. 16) in order to dial a dose, the switch 216 electrically couples the first and second helical tracks 300, 308 to one another (if they were not previously coupled). The processor 202 then determines the absolute rotational position of the encoded member 406 by causing a voltage to be applied to a first contact (for example, contact 212a) and then analysing which of the remaining six contacts are energised. It should be remembered that for each rotational position of the encoded member 406 at least two contacts 212a-212g engage a conductive segment 302 of the first helical track 300. Thus when a voltage is applied to the first contact 212a if any of the remaining six contacts 212b-212g are energised then both the first contact and the other energised contacts are associated with a code value of "1". The contacts that are not energised are associated with a code value of "0".

Due to the electrical connection between the first and second helical tracks 300, 308 if the first contact 212a is associated with a code value of "1" then the mode-shift contact 212i will also be energised when a voltage is applied to the first contact 212a. This enables the processor 202 to determine that the drug delivery device 100 is in dialling mode. Using the measured code values to determine the seven bit code associated with the rotational position of the encoded member 406, the processor 202 can thus determine the dialled dose for example by consulting a lookup table stored in the ROM 204.

However, if when a voltage is applied to the first contact (for example contact 212a) none of the other seven contacts 212b-212g are energised then the processor 202 instead applies a voltage to another one of the contacts (for example, the second contact 212b in FIG. 16). The processor then determines whether any of the other contacts 212a and 212c-212g are energised upon applying a voltage to the second contact 212b. This process is repeated for respective contacts, namely contacts 212a-212g, until at least one of the seven contacts 212a-212g is detected as being energised upon application of a voltage to another one of those contacts. When this is detected, since in the dialling mode the switch 216 electrically couples the first and second helical tracks 300, 308 then the mode-shift contact 212i will also be energised. Detecting this enables the processor 202 to determine that the drug delivery device 100 is in dose dialling mode. Furthermore, the processor 202 uses the seven bit code associated with the absolute rotational position of the encoded member 406 to determine the dialled dose in the foregoing manner.

Operation of the device 100 in dialling mode will now be briefly summarised. When a voltage is applied to one of the seven contacts 212a-212g, if any other contact and the mode-shift contact 212i are energised then the processor 202 can determine i) the seven bit code associated with the rotational position of the encoded member 406 and ii) knowledge that the device is in dialling mode. This information enables the processor 202 to determine the dialled dose for example by searching a lookup table stored in the ROM 204, the lookup table providing a conversion from the seven bit binary code result to a dose unit dialled. Also it is envisaged that the processor 202 may be configured to control the display 210 to show specific symbol(s) or text to indicate to a user of the device 100 that the device is in dialling mode.

In addition to (or instead of) determining a dialled dose, a drug delivery device 100 of the present embodiment may be configured to determine an amount of dose that has been dispensed. For example, when the dose delivery button 416 is pressed the switch 216 may electrically decouple the first and second helical tracks 300, 308. When an amount of dose has been dispensed the processor 202 may determine the position of the encoded member 406 relative to the housing 102 (i.e. by determining the seven bit binary code associated with the rotational position of the encoded member 406). Since the first and second helical tracks 300, 308 are electrically isolated when a dose is being dispensed, applying a voltage to any of the seven contacts 212a-212g to determine the aforementioned seven bit code will not cause the mode-shift contact 212i to become energised. This enables the processor to determine that the drug delivery device 100 is in dispensing mode. It is envisaged that the processor 202 may be configured to control the display 210 to show specific symbol(s) or text to indicate to a user of the device 100 that the device is in dispensing mode.

In other words when the seven bit code associated with a rotational position of the encoded member 406 is being determined, if the mode-shift contact 212i is not detected as being energised then the drug delivery device 100 is determined by the processor 202 to be in dispensing mode. The dose amount associated with such a binary code may be determined from a lookup table and compared with the dialled dose (i.e. the dose originally intended to be dispensed). The processor 202 may determine the dose which has been dispensed (or is yet to be dispensed, if any) by subtracting a remaining dose amount from the initially dialled dose. The display 210 may be used to show the dose amount yet to be dispensed if for any reason a user does not dispense the full amount of a dialled dose.

Having determined the drug dose which has been dispensed, the processor 202 may store the result in the flash memory 205. As mentioned above the display 210 may be controlled to display the result of the dispensed dose determination. The display 210 may display the result of the dispensed dose determination for a predetermined time, for example 60 seconds. Alternatively or in addition, the dispensed dose history may be retrieved electronically from the flash memory 205 by a user of the device 100 or by a health care professional. During dialling of the device 100 the dialled dose may be indicated to the user in any conventional way, for example by use of numerals printed on the encoded member 406. In some other embodiments, the dialled dose is not determined or indicated to the user.

Figure 17A:
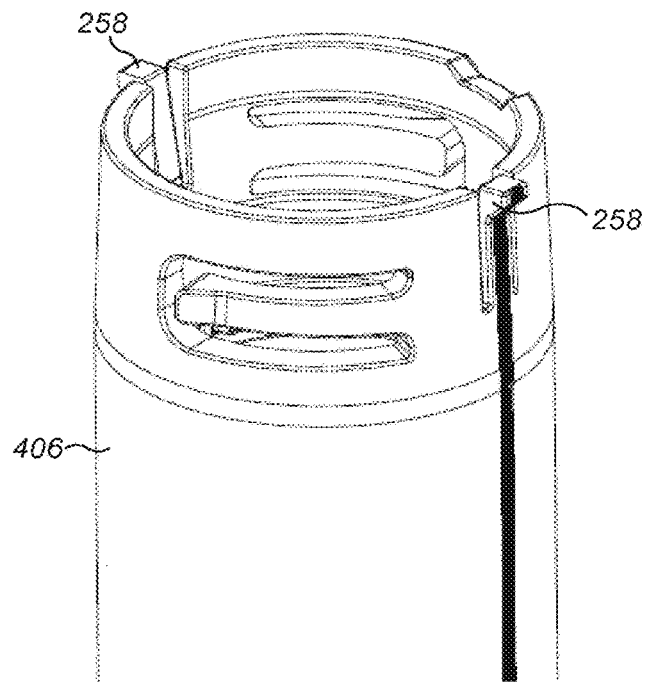
FIG. 17a shows an encoded member 406 which comprises part of a switch 216.
Figure 17B:
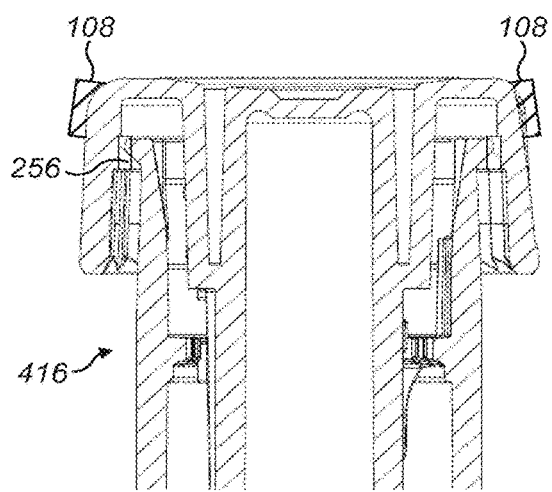
FIG. 17b shows a cross-sectional view of a switch 216 in a closed configuration.
Figure 17C:
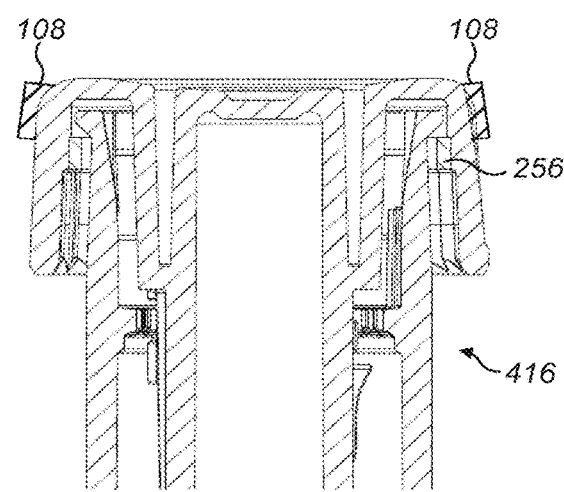
FIG. 17c shows the switch 216 in FIG. 17b in an open configuration.

One envisaged configuration of the switch 216 for electrically coupling and decoupling the first and second helical tracks 300, 308 will now be described with reference to FIGS. 17a to 17c. Such a switch 216 comprises part of a dose delivery button 416 and part of an encoded member 406. More specifically the aforementioned clutch is locked to the dose delivery button 416 comprising part of the switch 216, and the rotatable dial 108 is provided by a grip (such as a series of protruding parts) located on the outer surface of the button 416. Furthermore, a conductive ring 256 is positioned in a cavity defined by the dose delivery button 416 within which the encoded member 406 (FIG. 17a) is also received.

The encoded member 406 which comprises part of above mentioned switch 216 has two resiliently deformable arms 258. Part of the first helical track 300 is located on one deformable arm, and part of the second helical track 308 is located on the other deformable arm. When the dose delivery button 416 is not pressed by a user (for example in dialling mode), the conductive ring 256 is positioned in physical contact with the sections of track located on the deformable arms 258. In effect this closes the switch and the first and second helical tracks 300, 308 are electrically coupled. When the dose delivery button 416 is pressed however (for example in dispensing mode), the button 416 shifts relative to the encoded member 406 a distance such that the conductive ring 256 is brought out of physical contact with the sections of track on the resiliently deformable arms 258. In effect this closes the switch and the first and second helical tracks 300, 308 are electrically decoupled.

Further envisaged arrangements of the third embodiment described herein will now be briefly outlined.

Although a seven bit system has been described, the third embodiment is equally applicable for any number of position determining contacts greater than three, in other words at least contacts 212a-212d shown in FIG. 16. This is of course in addition to the mode-shift contact 212i. The seven bit system is preferred as it allows the full 0-80 unit dose range to be absolutely encoded.

The processor 202 may perform the process of checking the contacts 212a-212g and 212i while the encoded member 406 is actually rotating, i.e. while the device 100 is being dialled or is being used to dispense a substance. Alternatively the checking process may only be performed when the processor 202 detects that the encoded member 406 has been in a certain position for a predetermined amount of time (for example 100 milliseconds), thereby indicating that the device 100 has been dialled or dispensed an intended amount by a user.

Configuration of the switch 216 may also be reversed. For instance the switch 216 may be configured to electrically decouple the first and second helical tracks 300, 308 when the device 100 is idle or when a drug dose is being set by rotation of the rotatable dial 108. Such a switch 216 is configured to electrically couple the first and second helical tracks 300, 308 when the selected drug dose is being delivered. The switch 216 may be coupled to the dose delivery button 416 supported by the rotatable dial 108, such that when the button is depressed, the switch 216 connects the first and second helical tracks 300, 308.

Furthermore, the code defined by the first helical track 300 may have a different configuration, in particular it may define a different combination of "0"s and "1"s to the track shown in FIGS. 14 and 15.

Fourth Embodiment

Figures 18A, 18B:
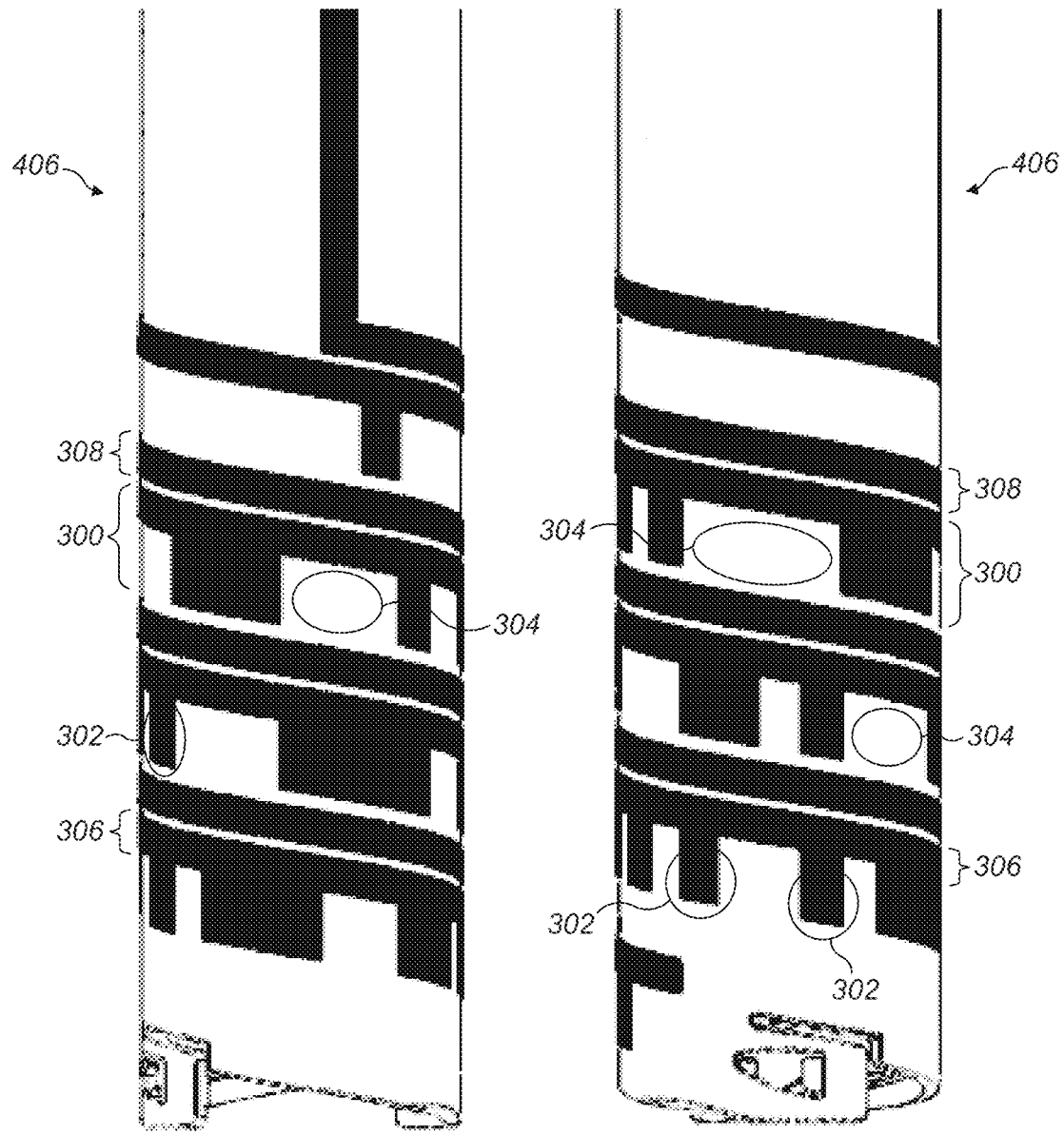
FIGS. 18a and 18b respectively show front and rear views of an encoded member 406 according to a fourth embodiment of the present invention.

FIGS. 18a & 18b illustrate front and reverse views of an encoded member 406 according to a fourth embodiment of the present invention. This encoded member 406 is similar to the embodiment shown in and described with reference to FIG. 12 in that it is also provided with a helical track 300 which forms an encoder, the track 300 having a relatively thicker power line 306. However in the present embodiment the encoded member 406 is also provided with an additional helical track 308 similar to the one illustrated in FIGS. 14a and 14b.

The additional track 308 shown in FIGS. 18a and 18b is configured to be engaged by an additional, ninth, contact, namely, a mode-shift contact 212i. This enables the processor 202 to determine whether a drug delivery device 100, according to a fourth embodiment thereof, is in dialling mode or dispensing mode.

As before when describing the third embodiment of the present invention, the helical track 300 shown in FIG. 18 will be referred to hereafter as the first helical track 300 and the additional track 308 will be referred to hereafter as the second helical track 308. It will be appreciated that the second helical track 308 essentially comprises a continuous electrically conductive member having the same pitch as the first helical track 300.

In order for the processor 202 of the present embodiment to determine whether the drug delivery device 100 is in dialling mode or dispensing mode, the device 100 is provided with the mode-shift contact 212i. Thus, in total, a drug delivery device 100 according to a fourth embodiment thereof is provided with nine contacts 212a-212i. For instance the seven contacts 212a-212g used to engage the conductive and non-conductive segments 302, 304 of the first helical track 300 during rotation of the encoded member 406. A power line contact 212h for engaging the power line 306 of the first helical track 300 during rotation of the encoded member 406. A mode-shift contact 212i for engaging the second helical track 308 during rotation of the encoded member 406.

An electrical conduction path (not shown) may join the first and second helical tracks 300, 308. The switch 216 (see FIG. 2) is disposed in this electrical conduction path. The switch 216 may be configured to connect electrically the first and second helical tracks 300, 308 when the device 100 is idle or when a drug dose is being set by rotation of the rotatable dial 108. The switch 216 may be configured to isolate electrically, or disconnect, the first and second helical tracks 300, 308 when the selected drug dose is being delivered. In particular the switch 216 may be coupled to the dose delivery button 416 supported by the rotatable dial 108 such that when the button is depressed the switch 216 disconnects the first and second helical tracks.

When a drug delivery device 100 according to the present embodiment is in use the processor 202 may determine the absolute rotational position of the encoded member 406 in the same manner heretofore described in connection with the second embodiment shown in FIG. 12. As in the second embodiment, the first helical track 300 and the contacts 212a-212g are arranged such that when a voltage is applied to the power line contact 212h at least one of the seven contacts 212a-212g is energised.

The processor 202 may be activated and controlled by software stored in the ROM 204 to cause the batteries 214 to apply a voltage to the first helical track 300 through the power line contact 212h. The processor may also execute a check on the seven contacts 212a-212g to determine the seven bit binary code associated with the absolute rotational position of the encoded member 406. Furthermore, in the present embodiment the processor 202 is additionally configured to determine the status of the switch 216 and hence whether the device 100 is in "dialling mode" or "dispensing mode".

The process of determining a dialled dose will now be described. When a user twists the rotatable dial 108 in order to dial a dose, the switch 216 electrically couples the first and second helical tracks 300, 308 shown in FIGS. 18a and 18b to one another (if they were not coupled previously). The processor 202 then determines the absolute rotational position of the encoded member by causing a voltage to be applied to the power line contact 212h and then analysing which of the seven contacts 212a-212g are energised. It should be remembered that for each rotational position of the encoded member 406 at least one contact 212a-212g engages a conductive segment 302 of the first helical track 300. Thus when a voltage is applied to the power line contact 212h at least one contact 212a-212g should be energised.

Any energised contacts are associated with a code value of "1". The contacts that are not energised are associated with a code value of "0". Due to the electrical connection between the first and second helical tracks 300, 308 applying a voltage to the first helical track 300 via the power line contact 212*h* will also cause the second helical track 308, and thus the mode-shift contact 212*i*, to be energised. This enables the processor 202 to determine that the drug delivery device 100 is in dialling mode. Using the foregoing code values to determine the seven bit code associated with the rotational position of the encoded member 406, the processor 202 can thus determine a dialled dose amount.

Operation of the device 100 in dialling mode will now be briefly summarised. In particular, in dialling mode when a voltage is applied to the power line contact 212*h* at least one of the seven contacts 212*a*-212*g* in addition to the mode-shift contact 212*i* will be energised. By analysing which contacts are energised at a particular point in time the processor 202 can determine i) the seven bit code associated with the absolute rotational position of the encoded member 406 and ii) knowledge that the device 100 is in dialling mode. This information enables the processor 202 to determine the dialled dose for example by searching a lookup table stored in the ROM 204, the lookup table providing a conversion from the seven bit binary code result to a dose unit dialled. It is also envisaged that the processor 202 may be configured to control the display 210 to show specific symbol(s) or text to indicate to a user of the device 100 that the device is in dialling mode.

In addition to (or instead of) determining a dialled dose, the drug delivery device 100 of the present embodiment may be configured to determine an amount of dose that has been dispensed. For example, when the dose delivery button 416 is pressed the switch 216 may electrically decouple the first and second helical tracks 300, 308. When an amount of dose has been dispensed the processor 202 may determine the position of the encoded member 406 relative to the housing 102 (i.e. by applying a voltage to the power line contact 212*h* and using contacts 212*a*-212*g* to determine the seven bit binary code associated with the rotational position of the encoded member 406). Since the first and second helical tracks 300, 308 are electrically isolated when a dose is being dispensed, applying a voltage to the power line contact 212*h* will not cause the mode-shift contact 212*i* to be energised. Detecting this as taking place enables the processor 202 to determine that the drug delivery device 100 is in dispensing mode. It is envisaged that the processor 202 may be configured to control the display 210 to show specific symbol(s) or text to indicate to a user of the device 100 that the device is in dispensing mode.

Operation of the device 100 in dispensing mode will now be briefly summarised. When the seven bit code associated with a rotational position of the encoded member 406 is determined, if the mode-shift contact 212*i* is not detected as being energised then the drug delivery device 100 is determined by the processor 202 to be in dispensing mode. The dose amount associated with such a binary code may be determined from a lookup table and compared with the dialled dose (i.e. the dose originally intended to be dispensed). The processor 202 may determine the dose which has been dispensed (or is yet to be dispensed, if any) by subtracting a remaining dose amount from the initially dialled dose. The display 210 may be used to show the dose amount yet to be dispensed if for any reason a user does not dispense the full amount of a dialled dose.

Having determined the drug dose which has been dispensed, the processor 202 may store the result in the flash memory 205. As mentioned above the display 210 may be controlled to display the result of the dispensed dose determination. The display 210 may display the result of the dispensed dose determination for a predetermined time, for example 60 seconds. Alternatively or in addition, the dispensed dose history may be retrieved electronically from the flash memory 205 by a user of the device 100 or by a health care professional. During dialling of the device, the dialled dose may be indicated to the user in any conventional way, for example by use of numerals printed on the encoded member. In some other embodiments, the dialled dose is not determined or indicated to the user.

It is envisaged that the switch 216 may have the same configuration as that previously described in connection with FIGS. 17*a* to 17*c*.

Further envisaged arrangements of the fourth embodiment described herein will now be briefly outlined.

Although a seven bit system has been described, the fourth embodiment is equally applicable for any number of position determining contacts greater than three, in other words at least contacts 212*a*-212*d*. This is of course in addition to the power line contact 212*h* and the mode-shift contact 212*i*. The seven bit system is preferred as it allows the full 0-80 unit dose range to be absolutely encoded.

The operation of the switch 216 may be reversed. In this alternative arrangement the switch 216 is configured to electrically decouple the first and second helical tracks 300, 308 when the device 100 is idle or when a drug dose is being set by rotation of the rotatable dial 108. The switch 216 is configured to electrically couple the first and second helical tracks 300, 308 when the selected drug dose is being delivered. The switch 216 may be coupled to the dose delivery button 416 supported by the rotatable dial 108 such that when the button is depressed the switch 216 connects the first and second helical tracks 300, 308.

The processor 202 may perform the process of checking the contacts 212*a*-212*g* and 212*i*, upon application of a voltage to the power line contact 212*h*, while the encoded member 406 is actually rotating i.e. while the device is being dialled or is being used to dispense a substance. Alternatively the checking process may only be performed when the processor 202 detects that the encoded member 406 has been in a certain position for a predetermined amount of time (for example 100 milliseconds), thereby indicating that the device has been dialled or dispensed an intended amount by a user.

Furthermore, the code defined by the first helical track 300 may have a different configuration, in particular it may define a different combination of "0"s and "1"s to the track 300 shown in FIGS. 18*a* and 18*b*. It is envisaged that the conductive and non-conductive segments 302, 304 may be arranged relative to the contacts 212*a*-212*g* to define a Gray code or a reflected binary code.

Fifth Embodiment

It will be appreciated that in the foregoing embodiments the seven bit encoding system defined by i) the helical track 300 and ii) the seven contacts 212*a*-212*g*, is what enables the absolute rotational position of the encoded member 406 to be determined (which thereby enables the dialled/dispensed dose amount to be determined). In light of this it is further envisaged that the seven bit encoding system need not necessarily be limited exclusively to electrically conductive members only.

Figure 19:
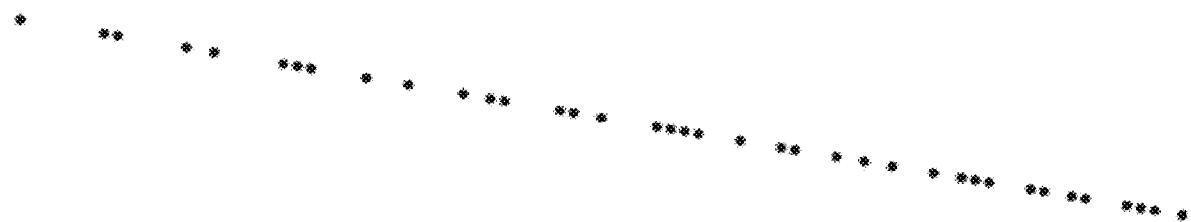
FIG. 19 shows an optically readable code suitable for use in manufacturing an encoded member according to a fifth embodiment of the present invention.

In a fifth embodiment of the present invention the seven bit coding system could alternatively comprise i) a series of markings (such as printed dots) forming an encoder on the outer surface 440 of an encoded member 406, such markings defining a code and ii) seven optical sensors. An unwrapped view of a track which defines such an optically readable code is illustrated in FIG. 19. The optically readable code defined by the track in FIG. 19 corresponds to the code defined by the helical track 300 shown in FIG. 9. More specifically, the optically readable code may be located on an encoded member 406 such that the markings (i.e. the printed dots for example) are located in similar positions to the conductive segments 302 in FIG. 7.

In such an arrangement the seven optical sensors may be positioned relative to the encoded member 406 in similar positions to the contacts 212a-212g in FIG. 8. For instance the optical sensors may be configured to analyse corresponding parts of the encoded member's outer surface 440 which the contacts 212a-212g otherwise engage in the embodiments previously described herein. The optical sensors may take any suitable form. The optical sensors are configured to provide an output signal that is different when a marking is present in the area of the optically readable code to an output signal that is provided when a marking is not present in the area of the optically readable code. In this way, the sensor output indicates whether or not a marker is present at the relevant location on the optically readable code. The optical sensors may be active (for instance including an illuminating light source) or they may be passive (relying on ambient light to detect the code).

An example of a suitable optical sensor arrangement comprises seven individual optical reflective type sensors arranged in a row. Since such sensors are of the reflective type they are used to analyse the intensity of light reflected from the encoded member's outer surface 440. It will be appreciated that the intensity of such reflected light changes depending on whether or not a marking is present in an area of optically readable code.

In a fifth embodiment of the drug delivery device 100, the processor 202 is configured to continually observe outputs of the optical sensors when determining the absolute rotational position of the encoded member 406 and thus the dose dialled or dispensed.

For instance by continually observing outputs of the optical sensors the processor 202 can determine the absolute rotational position of the encoded member 406 by directly analysing which optical sensors are directed towards a marking on the encoded member's outer surface 440. Such markings correspond with the conductive segments 302 previously described and the spaces between the optically readable markings correspond with the non-conductive segments 304 previously described.

When a user of a drug delivery device 100, according to a fifth embodiment thereof, rotates the rotatable dial 108 to set or dial in a drug dose, the processor 202 may be activated and may be controlled by software stored in the ROM 204 to apply a voltage to the optical sensors. The processor 202 may also be controlled by the software to execute a check on the optical sensors to determine which of them are directed towards a code marking (a printed dot for example) on the encoded member 406. This enables the seven bit binary code associated with the absolute rotational position of the encoded member 406 to be directly determined by the processor 202. In the present embodiment the optical sensors are may be arranged such that in each rotational position of the encoded member 406 at least one optical sensor is directed towards a code marking. In particular, those sensors detected as being directed towards a code marking are associated with a code value of "1". The sensors directed towards a space between code markings are associated with a code value of "0". Comparing this binary code with a lookup table in the manner heretofore described enables an amount of dose dialled to be determined. Similarly an amount of dose that has been dispensed (or is yet to be dispensed, if any) may be determined in a corresponding manner.

Additional envisaged arrangements of the fifth embodiment described herein will now be briefly outlined.

Although a seven bit system has been described, the fifth embodiment is equally applicable for any number of optical sensors greater than three. The seven bit system is preferred as it allows the full 0-80 unit dose range to be absolutely encoded.

The processor 202 may perform the process of checking the optical sensors while the encoded member 406 is actually rotating i.e. while the device 100 is being dialled or is being used to dispense a substance. Alternatively the checking process may only be performed when the processor 202 detects that the encoded member 406 has been in a certain position for a predetermined amount of time (for example 100 milliseconds), thereby indicating that the device has been dialled or dispensed an intended amount by a user.

Figure 22:
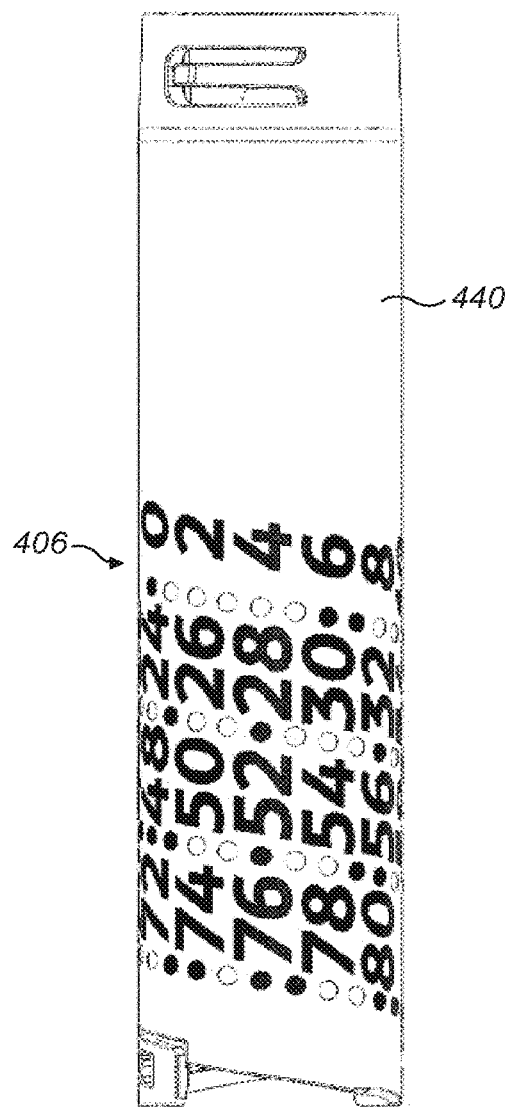
FIG. 22 shows another encoded member provided with the code in FIG. 19.

The optically readable code (such as the one in FIG. 19) may be located within the tick marks of a number scale presented on the encoded member 406 as shown in FIG. 22. Here the filled (black) circles represent "1" code values and the unfilled (white) circles represent "0" code values.

Furthermore, the code defined by the optically readable helical track may have a different configuration, in particular it may define a different combination of "0"s and "1"s to the track shown in FIG. 19. It is envisaged that the optically readable helical track may be arranged relative to the optical sensors to define a Gray code or a reflected binary code.

Sixth Embodiment

Figure 20:
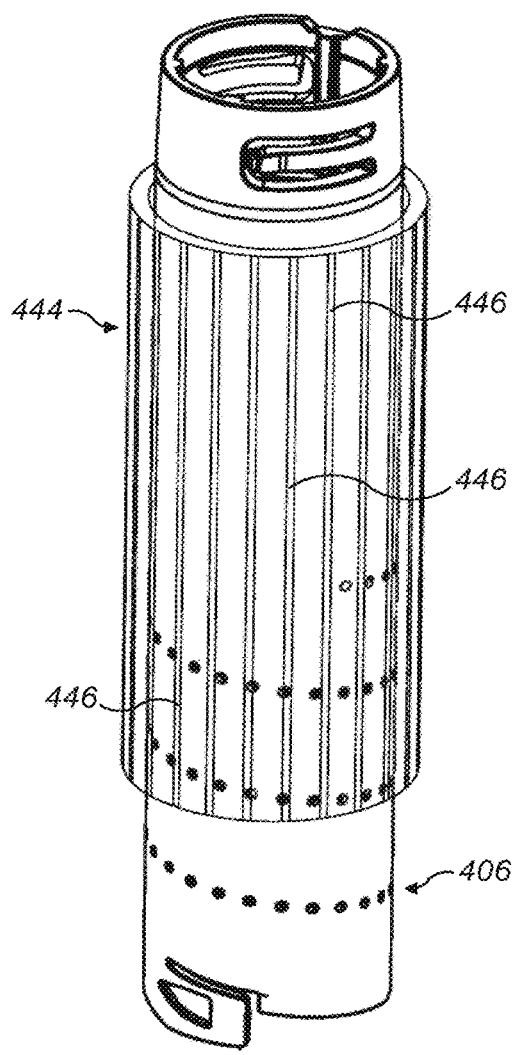
FIG. 20 shows an encoded member 406 according to a sixth embodiment of the present invention.

With reference to FIG. 20, a sixth embodiment of the drug delivery device 100 differs from the previously described fifth embodiment in that the device also has a mode-shift sleeve 444 located around at least part of the encoded member 406.

At least one of the optical sensors in the sixth embodiment should (as in the fifth embodiment) be capable of detecting optically readable code on the encoded member's outer surface 440. Such sensors will be referred to hereafter as code-detecting sensors.

Additionally however the drug delivery device 100, according to a sixth embodiment thereof, is capable of processing image data acquired by at least one optical sensor to determine the position of opaque lines 446 (or similar markings, for instance dashed or dotted lines) on the mode-shift sleeve 444. Optical sensors used for this purpose will be referred to hereafter as imaging devices and may comprise a camera for example. In particular, one or more imaging devices may be provided that process image data to determine the position of opaque lines 446. Alternatively however, the processor 202 may be used to process image data acquired by the or each imaging device in order to determine the position of opaque lines 446.

A suitable combination of optical sensors for the purposes of the sixth embodiment includes seven code-detecting sensors, such as the optical sensors heretofore described in connection with the fifth embodiment (i.e. seven individual optical reflective type sensors arranged in a row). In addition to these sensors however an imaging device is also provided that can be used to determine the position of opaque lines 446 on the mode-shift sleeve 444.

Looking at FIG. 20, a mode-shift sleeve 444 is sufficiently transparent for code-detecting sensors to detect the presence of code-defining markings located on the encoded member 406 therethrough. As already mentioned, a series of opaque lines 446 are provided on the mode-shift sleeve. The distance between such lines is no less than the width of a marking associated with a code value provided on the encoded member 406 (see FIG. 21). The sleeve 444 is arranged to rotate when a dose is dialled, but not to rotate when a dose is being dispensed. This may be achieved by coupling the mode-shift sleeve 444 to the dose delivery button 416. Thus when a user twists the dial 108 to set or dial in a dose, the sleeve 444 rotates with the dial 108. However, when a user presses the dose delivery button 416, since the button is configured to move only axially (without rotating) when a dose is being dispensed the mode-shift sleeve 444 moves axially also.

The movement of the opaque lines 446 across the field of view of the imaging device(s) can be used to determine the mode of operation of the drug delivery device 100. In view of the foregoing it will be appreciated that when a user twists the dial 108 to set or dial in a dose, the encoded member 406 is caused to rotate and the opaque lines 446 are caused to sweep across the field of view of the imaging device(s). Detecting the occurrence of such lines 446 sweeping across the field of view of the imaging device(s) enables the processor 202 to determine that the drug delivery device 100 is in dialling mode. Thus, analysing the code located on the encoded member 406 using the code-detecting sensor(s) allows the processor 202 to determine an amount of dose that has been dialled.

When a dose is being dispensed the opaque lines 446 are not caused to sweep across the field of view of the imaging device(s), however the encoded member 406 is caused to rotate in the manner heretofore described. Detecting the occurrence of only markings on the encoded member 406 sweeping across the field of view of the imaging device(s), and not the opaque lines 446, enables the processor 202 to determine that the drug delivery device 100 is in dispensing mode. Thus, analysing the code on the encoded member 406 using the code-detecting sensor(s) allows the processor 202 to determine an amount of dose that has been dispensed (or is yet to be dispensed, if any).

Figure 21:
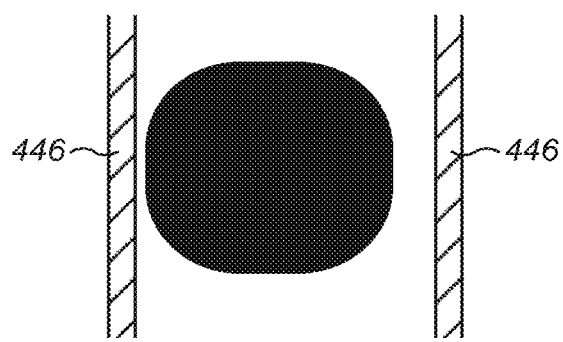
FIG. 21 shows two opaque lines 446 surrounding a marking which defines part of the code located on the encoded member 406 in FIG. 20.

The mode-shift sleeve 444 may be configured and arranged such that in each position of the encoded member that is associated with a unit of dose (0, 1, 2 . . . 80 International Units for example), the opaque lines 446 extend around markings which define the optically readable code as in FIG. 21. Furthermore, in each position of the encoded member that is associated with a unit of dose each opaque line 446 may be located in the field of view of at least one imaging device.

In embodiments that use conductive track, sensing of the presence or absence of track is performed using a contact and the processor. At a general level, this may involve hardware that compares a voltage signal provided by the contact with a threshold and indicting the presence or absence of track through an output that indicates whether the voltage exceeded or did not exceed respectively the threshold. In a processor implementation, it may involve buffering the signal provided by the contact, for instance using an inverter gate or other buffer, sampling the buffered signal and comparing the sampled signal to a reference. Other ways of sensing the presence or absence of track will be apparent to the skilled person.

Finally, it will be appreciated that the above described embodiments are purely illustrative and are not limiting on the scope of the invention. Other variations and modifications will be apparent to persons skilled in the art upon reading the present application. Moreover, the disclosure of the present application should be understood to include any novel features or any novel combination of features either explicitly or implicitly disclosed herein or any generalization thereof and during the prosecution of the present application or of any application derived therefrom, new claims may be formulated to cover any such features and/or combination of such features.

The invention claimed is:

1. A drug delivery device comprising:
a housing;
a cylindrical member rotatably supported within the housing and movable between a plurality of discrete positions;
a plurality of optical sensors;
a sleeve which surrounds at least part of the cylindrical member and which rotates relative to the optical sensors in one operational mode of the device but not in another operational mode of the device; and
an additional optical sensor for monitoring a rotational position of opaque markings provided on the sleeve in order to determine a mode of operation of the device;
wherein an outer surface of the cylindrical member is provided with a single track, the single track forming an encoder and having a plurality of first track segments and a plurality of second track segments arranged along a length of the single track, the first track segments and the second track segments respectively comprising differently marked parts of the single track;
wherein in each rotational position of the cylindrical member relative to the housing at least one different first track segment is capable of inducing a response in at least one of the optical sensors, thereby enabling a rotational position of the cylindrical member relative to the housing to be determined; and
wherein each discrete position of the plurality of optical sensors along the single track is associated with a unique binary code.

2. The device of claim 1, further comprising a processor configured to determine the rotational position of the cylindrical member relative to the housing by analyzing signals output from each of the optical sensors of the plurality of optical sensors which correspond with whether a first response or a second response is induced in a respective optical sensor in the plurality of optical sensors.

3. The device of claim 2, wherein the first track segments and the second track segments respectively comprise differently colored parts of the single track.

4. The device of claim 3, wherein the processor is configured to determine which of the plurality of optical sensors are directed towards a first track segment and which of the plurality of optical sensors are directed towards a second track segment, thereby enabling the rotational position of the cylindrical member relative to the housing to be determined.

5. The device of claim 2, wherein the processor is configured to determine a selected drug dose by searching a lookup table stored in a memory, the lookup table providing a conversion between the rotational position of the cylindrical member relative to the housing and a selected drug dose.

6. The device of claim 5, wherein the processor is configured to determine a delivered drug dose by subtracting a remaining drug dose from the selected drug dose.

7. The device of claim 1, wherein the cylindrical member is supported within the housing and configured to be rotated relative to the housing and the plurality of optical sensors.

8. The device of claim 1, wherein the cylindrical member is movable along a helical path between the plurality of discrete positions.

9. The device of claim 8, wherein each discrete position is being associated with a specific dose amount.

10. The device of claim 8, wherein in each discrete position of the cylindrical member each optical sensor of the plurality of optical sensors are respectively capable of having induced therein a first or second response by one of the first track segments or the second track segments.

11. The device of claim 8, wherein in each of the discrete positions of the cylindrical member a unique combination of first and second responses is capable of being induced across the plurality of optical sensors.

12. The device of claim 1, wherein the plurality of optical sensors are arranged along the single track.

13. The device of claim 12, wherein the plurality of optical sensors are configured to enable interaction with unique configurations of the first track segments and the second track segments.

14. The device of claim 13, wherein the plurality of optical sensors interact with unique configurations of the first track segments and the second track segments whenever an increment of insulin is dialed or dispensed.

* * * * *